(12) United States Patent
Bajic et al.

(10) Patent No.: US 11,535,897 B2
(45) Date of Patent: Dec. 27, 2022

(54) COMPOSITE EPIGENETIC BIOMARKERS FOR ACCURATE SCREENING, DIAGNOSIS AND PROGNOSIS OF COLORECTAL CANCER

(71) Applicant: King Abdullah University of Science and Technology, Thuwal (SA)

(72) Inventors: Vladimir Bajic, Thuwal (SA); Roberto Incitti, Thuwal (SA); Hicham Mansour, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 17 days.

(21) Appl. No.: 16/614,507

(22) PCT Filed: May 14, 2018

(86) PCT No.: PCT/IB2018/053358
§ 371 (c)(1),
(2) Date: Nov. 18, 2019

(87) PCT Pub. No.: WO2018/211404
PCT Pub. Date: Nov. 22, 2018

(65) Prior Publication Data
US 2020/0181716 A1 Jun. 11, 2020

Related U.S. Application Data

(60) Provisional application No. 62/507,333, filed on May 17, 2017.

(51) Int. Cl.
*C12Q 1/6886* (2018.01)
*C12Q 1/686* (2018.01)
*A61K 45/06* (2006.01)

(52) U.S. Cl.
CPC .......... *C12Q 1/6886* (2013.01); *C12Q 1/686* (2013.01); *A61K 45/06* (2013.01); *C12Q 2600/154* (2013.01)

(58) Field of Classification Search
None
See application file for complete search history.

(56) References Cited

U.S. PATENT DOCUMENTS 4,458,066 A    7/1984   Caruthers

FOREIGN PATENT DOCUMENTS

| WO | 2011126782 | 10/2011 |
| WO | 2012047899 | 4/2012 |
| WO | 2013033627 | 3/2013 |
| WO | 2015023285 | 2/2015 |
| WO | 2016109782 | 7/2016 |

OTHER PUBLICATIONS

Feng (PNAS 2010 vol. 107 No. 19 pp. 8689-8694) (Year: 2010).*
Beaucage, et al., "Deoxynuceloside Phosphoramidites—A New Class Of Key Intermediates For Deoxypolynucleotide Synthesis", Tetrahedron Letters, 22: 1859-1862, (1981).
Chatterjee, et al., "Comparison of alignment software for genome-wide bisulphite sequence data", Nucleic Acids Res., 40(10):e79 (2012).
Conner, et al., "Detection of sickle cell beta S-goblin allele by hybridization with synthetic oligonucleotides", Proc. Natl. Acad. Sci. USA, 80(1):278-282 (1983).
Eads, et al., "CpG Island Hypermethylation in Human colorectal Tumors Is Not associated with DNA Mehtyltransferase overexpression", Cancer Res. 59:2302-2306, (1999).
Eaton, et al., "Ribonucleosides and RNA", Ann. Rev. Biochem., 64:837-863 (1995).
Ferlay, et al., "Estimates of worldwide burden of cancer in 2008 Globocan 2008", International Journal of Cancer, 127:2893-2917 (2010).
Frommer, et al., "Agenomic sequencing protocol that yields a positive display of 5-methylcytosine residues in individual DNA strands", Proc. Natl. Acad. Sci., 89(5):1827-1831 (1992).
Gonzalgo, et al., "Rapid quantitation of methylation differences at specific sites using methylation-sensitive single nucleotide primer extension (Ms-SNuPE)", Nucleic Acids Res., 25:2529-2531 (1997).
Green, et al., "Nuclease-resistant nucleic acid ligands to vascular permeability factor/vascular endothelial growth factor", Chem. & Biol., 2:683-695 (1995).
Gyparaki, et al., "DNA methylation biomarkers as diagnostic and prognostic tools in colorectal cancer", J. of Molec. Med., 91:1249-1256 (2013).
International Search Report for corresponding PCT application PCT/IB2018/053358 dated Sep. 10, 2018.
Klobmann, et al., "Mirror-image RNA that binds D-adenosine", Nature Biotechnol., 14: 1112-1115 (1996).
Kok-Sin, et al., "Identification of diagnostics markers in colorectal cancer via integrative epigenomics and genomics data", Oncology Reports, 34(1):22-32 (2015).
Kuhn Hoffmann-Berling, et al., "DNA Helicases", CSH-Quantitative Biology, 43:63-67 (1978).
Landegren, et al., "A ligase-mediated gene detection technique", Science, 241(4869): 1077-1080 (1988).
Landegren, et al., "DNA diagnostics—molecular techniques and automation", Science, 242:229-237 (1988).

(Continued)

*Primary Examiner* — Katherine D Salmon
(74) *Attorney, Agent, or Firm* — Pabst Patent Group LLP

(57) ABSTRACT

The present disclosure concerns particular biomarkers for screening, diagnosing and/or prognosticating colorectal cancer, in particular in an accurate manner. The methods and compositions concern analysis of methylation patterns of one or more of 176 methylatable genomic DNA regions identified as described herein. In particular embodiments there are methods of detecting methylatable regions in genomic sequences.

10 Claims, No Drawings

Specification includes a Sequence Listing.

(56) References Cited

OTHER PUBLICATIONS

Lee, et al., "Aberrant Methylation of APC, MGMT, RASSF2A, and Wif-1 genes in Plasma as a Biomarker for Early Detection of Colorectal Cancer", Clin. Can. Res., 15(19):6185-6191 (2009).

Li, et al., "Sensitive digital quantification of DNA methylation inn clinical samples", Nature Biotechnol., 27(9): 858-863 (2009).

Nolte, et al., "Mirror-design of L-oligonucleotide ligands binding to L-arginine", Nature Biotechnol., 14: 1116-1119 (1996).

Pagratis, et al., "Potent 2'-amino-and 2'fluoro-2'-deoxyribonuceotide RNA inhibitors of keratinocyte growth factor", Nature Biotechnology, 15:68-73 (1997).

Radding, et al., "Homologous pairing and strand exchange in genetic recombination", Ann. Rev. Genetics, 16:405-437 (1982).

Reed, et al., "Antisense-mediated Inhibition of BCL2 Protooncogene Expression and Leukemic Cell Growth and Survival: Comparisons of Phosphodiester and Phosphorothioate Oligodeoxynucleotides", Cancer Res., 50:6565-6570 (1990).

Remontet, et al., "Cancer incidence and mortality in France over the period 1978-2000", Revue d'epidemiologie et de sante publique, 51(Pt.1):3-30 (2003).

Robertson, et al., "Stool DNA and Colorectal-Cancer Screening", N Eng. J. Med., 370(14): 1287-97 (2014).

Sadri, et al., "Rapid analysis of DNA methylation using new restriction enzyme sites created by bisulfite modification", Nucl. Acids Res., 24:5058-5059 (1996).

Saiki, et al., "A Novel Method for the Detection of Polymorphic Restriction sites by the Cleavage of Oligonucleotide Probes: Application to Sickle-Cell Anemia", Biotechnology, 3:1008-1012 (1985).

Strambu, et al., "Translating clinical research of Molecular Biology into a personalized, multidisciplinary approach of colorectal cancer patients", J. Med. Life, 7(1):17-26 (2014).

Tam, et al., "Biological availability and nuclease resistance extend the in vitro activity of a phosphorothioate-3'hyrdoxyypropylamine oligonucleotide", Nucl. Acids Res., 22:977-986 (1994).

Toyota, et al., "DNA methylation changes in gastrointestinal disease", Cancer Res., 59:2307-12 (1999).

Xiong, et al., "COBRA: a sensitive and quantitative DNA methylation assay", Nucleic Acids Res., 25(12):2532-2534 (1997).

* cited by examiner

COMPOSITE EPIGENETIC BIOMARKERS FOR ACCURATE SCREENING, DIAGNOSIS AND PROGNOSIS OF COLORECTAL CANCER

CROSS-REFERENCE TO RELATED APPLICATIONS

This application is a National Phase application under 35 U.S.C. § 371 of International Application No. PCT/IB2018/053358, filed on May 14, 2018, entitled "COMPOSITE EPIGENETIC BIOMARKERS FOR ACCURATE SCREENING, DIAGNOSIS AND PROGNOSIS OF COLORECTAL CANCER", which claims benefit of and priority to US Provisional Patent Application No. 62/507,333, filed on May 17, 2017, which where permissible are incorporated by reference in their entirety.

REFERENCE TO SEQUENCE LISTING

The Sequence Listing submitted May 14, 2018, as a text file named "64673019PCT-seq1-000001.txt," created on May 14, 2018, and having a size of 5,000 bytes is hereby incorporated by reference.

TECHNICAL FIELD

The invention is generally directed to the fields of molecular biology, cell biology, and medicine, including genetic diagnostics.

BACKGROUND OF THE INVENTION

Despite an increasing body of knowledge and the growing development of specific therapies and diagnostic tools, colorectal cancer (CRC) remains the second leading cause of malignant mortality in industrialized nations, accounting for more than 13% of all cancer deaths (Remontet et al. 2003; Globocan 2008). The relative survival rates (ratio of observed survival over the expected survival in a group of people with the same gender and age) depend on the stage of CRC at diagnosis. Stage I tumors are associated with the highest relative survival rate, while those of stage IV, known as poor prognosis (cancer.org/cancer/colonandrectumcancer/detailedguide/colorectal-cancer-survival-rates) with the lowest survival rate. Unfortunately, most cases of CRC are diagnosed at advanced stages, when a curative surgical treatment is not possible, and chemotherapy remains the only option in spite of high costs and undesirable side effects. Because of the absence of efficient screening and diagnostic methods of CRC, patients with colorectal neoplasia would most benefit from efficient early detection CRC tests that can reveal early stages of CRC, thereby enabling preventive interventions.

The risk of CRC begins to increase after the age of 50; thereafter, the risk continues to rise, approximately doubling with each succeeding decade. Increased risk is slower in women and, before age 75, women have a lower incidence of CRC than men. The desirable tests include as many as possible of the following features: average-risk, asymptomatic or symptomatic individuals, highly sensitive, non-invasive, low-risk, cost-effective, and ease of implementation across a large population. The first non-invasive genetic test approved by the FDA, detects 92% of CRCs and 42% of advanced adenomas. However, the specificity of it is less accurate and gives a negative screening result only for 87% of the normal subjects (Imperiale et al. *N Engl J Med.*, 370(14):1287-97 (2014)).

In many European countries, such as France, the HEMOCCULT® gaiac test or the fecal immunological test (FIT) is currently recommended in screening campaigns as the first step: tests on stool samples to detect occult blood. If the results are positive, this is followed by a second step: a colonoscopy to detect colorectal tumors. In the USA, these tools are recommended for screening. In the field of screening, blood tests are generally better accepted than fecal tests. However, the only formal serum test currently available is COLOVANTAGE® based on methylated Septin 9, but has poor performance for CRC (Gyparaki M T et al. 2013).

DNA methylation plays a substantial role in CRC development. It induces a change of transcriptome profile in epithelial colon cells. The down-regulation of some genes is induced by the methylation mechanism of CpG islands in their promoters, which inhibits the ability of transcription factors to induce the expression of their target genes. In addition to the role of the involvement of methylation mechanism in the genomic instability of colon epithelial cells during the CRC development, the methylation pattern of some genes is useful to screen and detect patients having different stages of CRC. A convenience is that such methylation tests can be done using body fluids, such as serum and others.

The present disclosure satisfies a need in the art to provide biomarkers for CRC screening that are both highly sensitive and highly specific.

BRIEF SUMMARY

Methods and compositions for screening, diagnosis, and/or prognosis of cancer, including CRC are provided. In some embodiments, the methods are non-invasive for CRC.

The cancer may occur in a human, although other mammals are encompassed in the disclosure, including dogs, cats, horses, and so forth.

Certain embodiments provide methods and compositions for CRC screening, diagnosis and/or prognosis using particular methylation level of Methylatable Regions (MRs) of genomic DNA sequence. An MR refers to a DNA region of 50 nucleotides in length. The term "methylation level" of an MR refers to the number of methylated residues within an MR. In specific embodiments, the specific MRs serve as biomarkers for CRC screening, diagnosis and/or prognosis. The methylation level of these markers is tested in a sample containing DNA from a subject. The sample can be tissue or body fluids (such as serum, plasma, urine, spittle, sputum and/or stool, for example) of patients with CRC, or of patients suspected of having CRC. The set of 176 MRs disclosed herein serves as a set of epigenetic biomarkers. For a given patient, the total methylation (mTOT) is the sum of the methylation levels of all measured MRs from the set of 176 MRs. The coverage (COV) of a patient by the methylated MRs is the number of measured MRs from the set of 176 MRs that contain at least one methylated residue. For a given patient a methylation score (mSCORE) is defined as follows:

$$mSCORE = COV \times mTOT \quad (1)$$

The mSCORE can be used to determine the presence of cancerous lesions. If mSCORE=0 (in other words, if none of 176 MRs is methylated) then the subject does not have CRC. If one or more of the MRs are methylated, the subject may develop CRC or may already have CRC. If particular additional conditions are satisfied, e.g. mSCORE is greater than a specific threshold, the patient can be diagnosed with very high accuracy of having or developing CRC. A list of MRs is provided in Table 1. These MRs are target regions for the analysis described herein.

Thus, in specific embodiments, the methylation of one or more MRs is suggestive of the CRC presence in a subject or a potential for a subject to develop CRC. In some embodiments, one can use combinations of the methylation levels of these MRs and known anomalies/characteristics of cancers and specifically CRC, such as KRAS and BRAF mutations, microsatellites deficiencies, or carcinoembryonic antigen (CEA) tests (Strambu et al. 2014), to significantly improve accuracy of screening, diagnosis and/or prognosis of CRC.

In some embodiments, the methylation score that is above a specific threshold for a subject provides screening, diagnostic and prognostic tests for CRC.

The disclosed methods may employ assaying tissue, blood, serum, plasma, spittle, stool, urine, or any other body fluid containing DNA. Methods to assess the target directly in a bio-specimen are known in the art. Alternatively, an extract may be assessed and nucleic acids can be concentrated from body fluids, using conventional techniques such as silica chromatography, silica beads, phenol chloroform method, or any beads or columns enabled to concentrate nucleic acids. Methods to target the specific nucleic acids that correspond to the particular region using normal or labeled oligonucleotides are known in the art and include SYBER® green, High Resolution Melt analysis, TAQMAN® assays or Fluorescence Resonance Energy Transfer (FRET) for example. Methods to ascertain the level of methylation of the target sequences or MRs are known in the art and include, for example, MethyLight PCR (such as AB, Roche, Qiagen; Valencia, Calif.), methylation array (nlurnina, Agilent, Affymetrix), methylation sequencing (Illumina, AB, Roche, Helicos, Pacific Bio), methyl-bearing (using flow cytometry), mass spectrometry, bisulfite sequencing, or a combination thereof.

The present disclosure includes screening, diagnosing, and/or prognosing CRC by assaying methylation level of 176 MRs, wherein (a) the methylation of any one of the 176 MRs in a subject is suggestive of a potential CRC presence or a potential to develop CRC, (b) where CRC is detected if specific additional conditions are satisfied, and (c) when there is no CRC if none of the 176 MRs is methylated.

One embodiment provides a method performed as part of a regular checkup or physical examination. Therefore, in certain aspects the subject has not been diagnosed with cancer, and typically for those particular embodiments it is not known that a subject has a hyperproliferative disorder, such as a colorectal neoplasm. In other embodiments the individual is at risk for CRC, is suspected of having CRC, or has a personal or family history of cancer, including CRC, for example. In some cases, an individual is known to have cancer and undergoes methods of the invention to determine the type of CRC, staging of CRC, treatment response to CRC, and/or prognosis. In other cases, the individual has already been diagnosed for CRC cancer and may be subjected to surgery for CRC cancer resection and may undergo methods of the invention to survey the recurrence of polyps or CRC.

In alternative embodiments, the methylation score obtained from 176 MRs for a subject, which is above defined thresholds, is indicative of CRC diagnosis, screening, and/or prognosis, and the methylation level may be determined by routine methods in the art.

In one embodiment, there is a method for screening, diagnosing, and/or prognosing CRC in a subject, comprising one or more steps of obtaining a sample from the subject; and assaying the sample for methylation level of one or more of 176 MRs, and where MRs are selected from the human genome version GRCh37/hg19 following orientation of the strand and where the locations of these MRs are described by the information in Table 1. In specific cases, the methylation score of a subject is compared to a standard, and the standard can be derived from the methylation score value from a sample from a subject that does not have CRC or the standard can be derived from the methylation score value from a cancerous sample, which may be selected from the group consisting of tissue, blood, spittle, serum, plasma, urine, sputum, biopsy and stool.

Individuals subjected to methods of the disclosure include those that are typically 50 years or older in age, as an example, and the individual may or may not have a prior history of cancer. In some aspects, the individual has one or more symptoms of CRC or may be asymptomatic for CRC. Symptoms include a change in bowel habits, constipation that lasts more than a couple of weeks, diarrhea that lasts more than a couple of weeks, a feeling that the bowel does not empty completely, blood in the stool, narrow or thinner than normal stool, abdominal discomfort, gas pains, bloating, fullness, cramps, weight loss, fatigue, anemia, and a combination thereof. In specific embodiments, the individual has a personal or family history of CRC, has or has had colon polyps, bowel inflammatory disease, or is or was positive for hemoccult test. The individual may have a personal or family history of familial adenomatous polyposis, Lynch syndrome, Peutz-Jeghers syndrome or juvenile polyposis syndrome. In some cases, the individual is subjected to one or more other assays for determination of CRC, including such assays as one selected from the group consisting of stool testing, barium enema, virtual colonoscopy, sigmoidoscopy, and colonoscopy.

In specific embodiments, the individual is diagnosed as having CRC. In specific embodiments, when an individual is diagnosed as having CRC, the individual has CRC stage 0, 1, 2, 3, or 4. In certain cases, following a positive diagnosis for CRC, the individual is treated for CRC, and such treatment may include surgery, chemotherapy, radiation, gene therapy, or a combination thereof. The chemotherapy may be selected from a group comprising fluorouracil, bevacizumab, irinotecan, capecitabine, cetuximab, oxaliplatin, cetuximab leucovorin, panitumumab, and a combination thereof. In specific embodiments, the chemotherapy modifies methylation level of some of the MRs. The exact causal mechanism of the modification is not fully understood, but one can measure the effects in a consistent way by state-of-the-art technology (QPCR, Met-Seq NGS sequencing, etc.).

In one embodiment, there is a substrate, comprising nucleic acids, each comprising part or all of MRs or nucleic acids that are complementary thereto, and in some cases the substrate is further defined as a microchip.

In another embodiment, there is provided a method for screening, diagnosing, and/or prognosticating CRC in an individual, comprising one or more of the steps of: obtaining a sample from the individual; and assaying the sample for methylation level of one or more MRs.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

For a more complete understanding of the present invention, reference is now made to the following descriptions.

Definitions of certain terms in the disclosure are provided as follows:

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "comprise essentially" or "comprise" one or more sequences of the invention, for example. Some embodiments of the invention may comprise or comprise essentially one or more elements, method steps, and/or methods of the invention. It is contemplated that any method or composition described herein can be implemented with respect to any other method or composition described herein. Embodiments discussed in the context of methods and/or compositions of the invention may be employed with respect to any other method or composition described herein. Thus, an embodiment pertaining to one method or composition may be applied to other methods and compositions of the invention as well.

As used in this application, the terms "about" and "approximately" are used as equivalents. Any numerals used in this application with or without about/approximately are meant to cover any normal fluctuations appreciated by one of ordinary skill in the relevant art.

Determine: Several of the methods described herein may include a step of "determining". Those of ordinary skill in the art, reading the present specification, will appreciate that such "determining" can utilize any of a variety of techniques available to those skilled in the art, including for example specific techniques explicitly referred to herein. In some embodiments, a determination involves manipulation of a physical sample. In some embodiments, a determination involves consideration and/or manipulation of data or information, for example utilizing a computer or other processing unit adapted to perform a relevant analysis. In some embodiments, a determination involves receiving relevant information and/or materials from a source.

Isolated: The term "isolated", as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, at least about 20%, at least about 30%, at least about 40%, at least about 50%, at least about 60%, at least about 70%, at least about 80%, at least about 90%, or more of the other components with which they were initially associated. In some embodiments, isolated agents are more than 90%, 91%, 92%, 93%, 94%, 95%, 96%, 97%, 98%, 99% pure.

Nucleic acid molecule. The term "nucleic acid molecule" is used broadly to mean any polymer of two or more nucleotides, which are linked by a covalent bond such as a phosphodiester bond, a thioester bond, or any of various other bonds known in the art as useful and effective for linking nucleotides. Such nucleic acid molecules can be linear, circular or supercoiled, and can be single stranded or double stranded, e.g. single stranded or double stranded DNA, RNA or DNA/RNA hybrid. In some embodiments, nucleic acid molecules are or include nucleic acid analogs that are less susceptible to degradation by nucleases than are DNA and/or RNA. For example, RNA molecules containing 2"-O-methylpurine substitutions on the ribose residues and short phosphorothioate caps at the 3'- and 5'-ends exhibit enhanced resistance to nucleases (Green et al., Chem. Biol., 2:683-695 (1995), which is incorporated herein by reference). Similarly, RNA containing 2'-amino-2'-deoxypyrimidines or 2'-fluro-2'-deoxypyrimidines also exhibit resistance to nucleases (Pagratis, et al., Nature Biotechnology, 15:68-73 (1997), which is incorporated herein by reference). Furthermore, L-RNA, which is a stereoisomer of naturally occurring D-RNA, is resistant to nuclease activity (Nolte et al., Nature Biotechnol., 14:1116-1119 (1996); Klobmann et al., Nature Biotechnol., 14:1112-1115 (1996); each of which is incorporated herein by reference). Such RNA molecules and methods of producing them are well known in the art and can be considered to be routine (see Eaton and Piekern, Ann. Rev. Biochem., 64:837-863 (1995), which is incorporated herein by reference). DNA molecules containing phosphorothioate linked oligodeoxynucleotides are nuclease resistant (Reed et al., Cancer Res. 50:6565-6570 (1990), which is incorporated herein by reference). Phosphorothioate-3' hydroxypropylamine modification of the phosphodiester bond also reduces the susceptibility of a DNA molecule to nuclease degradation (see Tam et al., Nucl. Acids Res., 22:977-986 (1994), which is incorporated herein by reference).

Organ or Tissue. As used herein, the terms "organ or tissue" and "selected organ or tissue" are used in the broadest sense to mean an organ or tissue in or from a body. In some embodiments, an organ or tissue has a pathology, for example, tissue containing tumors (including lung containing tumors), whether primary or metastatic lesions. In some embodiments, an organ or tissue is normal (e.g., healthy). The term "control organ or tissue" is used to mean an organ or tissue other than a selected organ or tissue of interest. In some embodiments, a control organ or tissue is characterized by the inability of a ligand-encoding phage to home to the control organ or tissue and, therefore, is useful for identifying selective binding of a molecule to a selected organ or tissue.

Sample: As used herein, the term "sample" refers to a cell, tissue, organ or portion thereof that is isolated from a body. It will be appreciated that a sample may be or comprise a single cell or a plurality of cells. In some embodiments, a sample is or comprises a histologic section or a specimen obtained by biopsy (e.g., surgical biopsy); in some embodiments, a sample is or comprises cells that are or have been placed in or adapted to tissue culture. In some embodiments, the sample is or comprises an intact organ or tissue. In some embodiments, the sample is or comprises circulating cells, such as circulating tumor cells. In some embodiments a sample is obtained by an individual that is performing the methylation assay, whereas in some embodiments a sample is obtained by an individual that is not performing the methylation assay. The obtaining of the sample encompasses extracting the sample itself from the individual being tested yet also encompasses retrieving the sample from its transmittal or from storage, either directly or indirectly. The sample may be from or be representative of sample from the colon and/or rectum Sample processing: As used herein, the term "sample processing" generally refers to various steps that may be accomplished to prepare a sample for quantification. In some embodiments, crude sample (e.g., whole tissue, homogenized tissue, paraffin-embedded tissue, etc.) is prepared. In some embodiments, purified or highly purified sample is prepared.

Subject: As used herein, the terms "subject," "individual" or "patient" refer to a human or a non-human mammalian subject. In some embodiments, a subject is a non-human primate. In some embodiments, the subject is a dog, cat, goat, horse, pig, mouse, rabbit, or the like. In some embodiments, a subject is a human. In some embodiments, a subject is healthy. In some embodiments, a subject is suffering from or susceptible to a disease, disorder or condition (e.g., associated with the endothelium). In some embodiments, a human subject is a patient having a surgical tumor resection or a surgical biopsy. In some embodiments, a human subject is overweight, obese, has a metabolic condition related to being overweight or obese, or has cancer, is suspected of having cancer, or is at risk for developing cancer.

The term "screening" as used herein denotes the following: On a population of individuals with known or unknown degree of risk of developing the disease, determining which individuals have to undergo more in-depth diagnostic investigation.

The term "diagnosing" as used herein denotes the disease's identification (e.g., by an authorized physician or a test approved from a health care authority).

The term "prognosing" as used herein denotes the forecasting of disease evolution. The term "Methylatable Region", denoted here as MR, is a DNA region of 50 nucleotides in length.

The term "methylation level" of an MR refers to the number of methylated residues in the MR.

The term "total methylation" of a patient, denoted here as mTOT, is the sum of methylation levels of all MRs measured for the patient.

The term "coverage" of a patient, denoted here as COV, is the number of MRs measured for the patient, which contain at least one methylated residue.

The term "methylation score", denoted here as mSCORE, for a patient is defined as a product of the patient's coverage and total methylation of 176 MRs, i.e. as:

$$mSCORE = COV \times mTOT \quad (1)$$

I. Methods for Diagnosing or Predicting Cancer

Methods and compositions suitable for CRC screening, diagnosis, and/or prognosis are provided. The methods include assaying 176 MRs, of genomic DNA for determining the number of methylated nucleotides in each of these MRs, which may be referred to herein as "markers" or "biomarkers." The presence of methylated nucleotides in MRs is suggestive of potential CRC. In some embodiments, the response to treatment for CRC, the prognosis with CRC, a combination thereof, and so forth can be determined by monitoring a change in methylation of specific MRs. For example, if some of the MRs of a subject's DNA are found to be methylated before treatment and are found to be un-methylated after treatment, the response to treatment may be considered favorable and the prognosis is favorable. Methylation of one or more of the MRs is suggestive of CRC or the likelihood of developing CRC. Absence of methylation of all 176 MRs indicates that there is no CRC.

The disclosed methods assist in accurate tumor diagnosis regardless of the stage of cancer, including at an early stage (stages I and II) of CRC in individuals. The methods of the disclosure allow an increase in the overall survival of CRC patients by accurately diagnosing or detecting cancer at early stages and thereby they contribute significantly to reducing the cost of patients supported by health authorities. Moreover, the methods of the disclosure are easy for routine clinical use by any medical testing/pathology laboratory.

The assaying may be employed as part of routine screening of an individual or may be employed upon indication that an individual either has or is at risk for having CRC or is in need of prognosis, response to treatment, recurrence survey, typing and/or staging of CRC, for example.

II. Genomic DNA Regions for Detecting or Diagnosing Cancer

The methylation of certain regions of genomic DNA has been discovered to be correlated with the presence or a high likelihood of developing CRC. These regions of genomic DNA can also be used for determining the risk of developing CRC, stage of CRC, type of CRC and/or monitoring of treatment for CRC.

In specific embodiments, the regions of genomic DNA are of a certain length, such as about 50 nucleotides (nt) or exactly 50 nt in length. Thus, in specific embodiments, the methylation of one or more of the region(s) is indicative of one or more aspects related to CRC. In certain embodiments, the target regions or methylatable regions (MRs) comprise a certain sequence that may be methylated, including at least one nucleotide. In specific embodiments, when a particular region is methylated, this methylation is indicative of CRC or CRC-related condition. In other embodiments when none of 176 MRs is methylated, the absence of CRC is confirmed.

Particular MRs are encompassed herein and disclosed in SEQ ID NOS:1-176 in Table 1. The MRs are located on different chromosomes within the genome and are 50 nt in length. However, in some cases the region of the MR that is methylatable is less than 50 nt and/or the region of the MR that is informative for an aspect of CRC is less than 50 nt. In certain embodiments, the region of the MR that is methylatable is combined with sequence that flanks the MR to be assayed and/or be informative. The methods of the disclosure may utilize all of the listed MR regions for methylation level analysis or the methods may use less than all of the listed MRs for analysis, including at least or no more than 1, 2, 3, 4, 5, 6, 7, 8, 9, 10, 20, 30, 40, 50, 75, 100, 125, 150, or 176 MRs for analysis.

In certain embodiments, the entirety of the MR is assayed for determining the number of methylated nucleotides, and thus the method(s) would assay the sequence consisting of one or more MRs of the disclosure. In some cases, the region of DNA that is assayed for methylation level includes some or all of the MR but also includes flanking sequence of the MR in the 5' direction, the 3' direction, or both. Such flanking regions extend up to but not including the first encountered CpG.

In certain embodiments for detecting the methylation level of one or more MRs, one can assay the MRs for sequence that is comprised in at least part of sequence of one or more of SEQ ID NOS:1-176. In such cases, to determine methylation of an MR, one examines the methylation level of every C within the MR boundaries that is part of a CpG, irrespective whether the associated G is part of the MR.

In specific embodiments, the region within one or more of SEQ ID NOS:1-176 is at least or no more than 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length.

Table 1 below provides exemplary MR utilized in methods and compositions of the disclosure. The MRs are in relation to human genome sequence hg19, and one of skill in the art would be able to correspond the noted nucleotide designations below to other human genome sequences based on the information below and the corresponding sequences in the sequence listing. The genomic coordinates provided below correspond to the forward strand and are counted from the beginning of the chromosome.

TABLE 1

Examples of Sequences of Particular MRs

| METHYLATABLE REGION | SEQUENCE IDENTIFIER |
|---|---|
| >chr10: 15761512-15761562<br>CGGGAGCGCCTTCGTCCCCGCGCGCACCTCCCCGGGTCGGGCGACTTACG | (SEQ ID NO: 1) |
| >chr10: 94825532-94825582<br>ACTTGAGATTTAATCGACTTCAAAACCGTACACACAGTCGCGGCGGTAAT | (SEQ ID NO: 2) |
| >chr10: 134599947-134599997<br>GGAAAGAATGCAGATTTGAGGACCCGCCCGCGCGCTCGGAGCGCCCCACT | (SEQ ID NO: 3) |
| >chr10: 133110457-133110507<br>CTGGGCTGCGGATCCGGCGCAGGCGGCCCCGGACGCTGCTAGGCGCGGGC | (SEQ ID NO: 4) |
| >chr10: 129537049-129537099<br>GGCACCTTCCCCGGGGGCCTGGCGGGCGACTTTTCTTTCGGGAGGCGGCC | (SEQ ID NO: 5) |
| >chr10: 21789279-21789329<br>GCGGGAGCCCCTTCCGGGGAACACGCTCTCCGGGCCGCGCAGCCGGGCGA | (SEQ ID NO: 6) |
| >chr11: 47376874-47376924<br>CCCGTCTTGCCGTAGTTGCGCAGCGCGCGCGCCATCTTCTGGTAGGTCAT | (SEQ ID NO: 7) |
| >chr11: 62370190-62370240<br>GGGCCCACCGGTCCCACCCCGGCGATCCCCGCGGCCTCACCTTGGCACGA | (SEQ ID NO: 8) |
| >chr11: 62370194-62370244<br>CCACCGGTCCCACCCCGGCGATCCCCGCGGCCTCACCTTGGCACGAGCGC | (SEQ ID NO: 9) |
| >chr11: 62370201-62370251<br>TCCCACCCCGGCGATCCCCGCGGCCTCACCTTGGCACGAGCGCACGGGTA | (SEQ ID NO: 10) |
| >chr12: 111472028-111472078<br>TCTACGGCGACTCCAGGTTAGTGCGGGCAGCGCCGGCCGCGCGGCCGTGA | (SEQ ID NO: 11) |
| >chr12: 5018771-5018821<br>TCCAATGTGAAATTCCCGGGGAAGGTCGCGAGCCGCTAGGGGCCGTTCGT | (SEQ ID NO: 12) |
| >chr12: 5019071-5019121<br>GAAATGGACCGAGCGGACCCGCCGCCGCACGCACCCTGCTCCACTCCAAG | (SEQ ID NO: 13) |
| >chr12: 5019121-5019171<br>CTCCTAAGGGCTCCTGGCGCGCCGCGTAGCCTTGGCGAGGTCCGCGCTGG | (SEQ ID NO: 14) |
| >chr12: 5019221-5019271<br>CCGCCCGCCTCCTTCGGGATCGAATCAAGGGCTCCCATAGTGTTAGGAGG | (SEQ ID NO: 15) |
| >chr12: 5019271-5019321<br>GGGCGAGAGTGCTGTTTATCGTCATTTGCCTCGGAGCTTCGAGAGAGGGT | (SEQ ID NO: 16) |
| >chr12: 5019321-5019371<br>GGTATTTTGCTTTTCCGCCCCGCATCCTCCGGAACTCCCTGCACCGGAGA | (SEQ ID NO: 17) |
| >chr12: 5019421-5019471<br>AGGAACATTTTCGCCGTAGCTGCTCCGTAAAGCGATTGTCCAACTGAGAG | (SEQ ID NO: 18) |
| >chr12: 5019471-5019521<br>GGGCGTCGGACGAGTGGACCAGGGCGGCGAGTTTGCCCGGCGCGTCTCGG | (SEQ ID NO: 19) |
| >chr12: 5019521-5019571<br>ATGCTGCTGCGGCGGCCGCCGCGGCTCCCGCCAGGGCACTGCAAAGACGA | (SEQ ID NO: 20) |
| >chr12: 5019671-5019721<br>GGGGGTTGGGGGGACCGGGTGGGGGAGGCCGGGGGTGCGGGATGCTGTC | (SEQ ID NO: 21) |
| >chr12: 5019721-5019771<br>CGGGACCCTGAGCTTCCCCCGGCGTCTCTCGGCGCTTTTCCGATCTCTAG | (SEQ ID NO: 22) |

TABLE 1-continued

Examples of Sequences of Particular MRs

| METHYLATABLE REGION | SEQUENCE IDENTIFIER |
|---|---|
| >chr12: 5019971-5020021<br>TTCTACCCCCGTATCACTTTCTATTTCTCTGCAGCGTGCATCGATCGCCC | (SEQ ID NO: 23) |
| >chr12: 5020421-5020471<br>TGGGCGTGAGGGAGACGCGCGCTCCGGTGGGGGGGCCGCTTGGGTCCCCC | (SEQ ID NO: 24) |
| >chr12: 5153335-5153385<br>TGGAGAACGGCGGTGCCATGACCGTCAGAGGAGGCGATGAGGCCCGGGCA | (SEQ ID NO: 25) |
| >chr12: 58131214-58131264<br>TTGCCTTTCCGAGGGGACAACTTCCCTCGGGCTCCAGCCCCAGCCCCGAC | (SEQ ID NO: 26) |
| >chr12: 4918892-4918942<br>GTCTTTTCGGGCAGCCAATTTCACACGCGCCTGTGTGCGGTTCCGGGCAT | (SEQ ID NO: 27) |
| >chr12: 4918942-4918992<br>CCCAGTAAGCTCTAGCACCCGGGCGCGGGTAACGGGAAGCGCAGAACCAA | (SEQ ID NO: 28) |
| >chr12: 4919192-4919242<br>CACCTCCGAGGGGGCATGAGATCGGAGAAATCCCTTACGCTGGCGGCGCC | (SEQ ID NO: 29) |
| >chr13: 111766866-111766916<br>TGTCATCAGTTGTTCGAGGAAGCTCGCGCATGACGCGACACTTGCCGTCT | (SEQ ID NO: 30) |
| >chr13: 111767116-111767166<br>GTGAGGTCGGCGCCGCGCTCCGGAGAGTCGGTTCCTCCCGATTCAGACCC | (SEQ ID NO: 31) |
| >chr13: 111767366-111767416<br>cggccaggggcgcggggcgcacggcgggcccggggcAGGTAAGCGCAGGT | (SEQ ID NO: 32) |
| >chr13: 111768316-111768366<br>GGGCTTCTGCGCCGCCCGAACGCTAAGTTGCCCCTCCGCGTGGGGGCCG | (SEQ ID NO: 33) |
| >chr13: 95354986-95355036<br>CCGGCGCCCCAGAGAAGTTCGGGGAGCGGTGAGCCTAGCCGCCGCGCGCT | (SEQ ID NO: 34) |
| >chr13: 95364136-95364186<br>GGCCGCTTCTCCGACTCTGTGAGCAGTTTCCACTCGGCGCCCAAGCGCTT | (SEQ ID NO: 35) |
| >chr13: 110960109-110960159<br>CACCGCGCTGTCCCCGCGTCTCGCGGACCGAGACCGGCGGTGAGGATGGG | (SEQ ID NO: 36) |
| >chr13: 110960259-110960309<br>GACCAGCGCGCGGTGGCCGGCCCTGCCCTACGGCGGTAAGCGACTTTCTG | (SEQ ID NO: 37) |
| >chr13: 110960459-110960509<br>GCGTCTTGGCGGTAAGTCCTGGCTCCCGCGCTTGGACTTGCGCGCCCGAG | (SEQ ID NO: 38) |
| >chr13: 96293997-96294047<br>CGCTGGGGGCGCACAGGCCATGGAGGCCGCACCCGCGGCGGCGGCGGCC | (SEQ ID NO: 39) |
| >chr13: 78493276-78493326<br>CAGCGCGCCCAGGAGTGCGCCGGAGATTCGGAAACCCGCAGAGACTTCTC | (SEQ ID NO: 40) |
| >chr13: 28498407-28498457<br>CGGAGCCGGAGGAGAACAAGCGGACGCGCACGGCCTACACGCGCGCACAG | (SEQ ID NO: 41) |
| >chr13: 25745579-25745629<br>ACGGCGGCTCGGCGGCCGGCGTTTCGGCGGCACAGTCACAATGCAAGTCC | (SEQ ID NO: 42) |
| >chr13: 25745679-25745729<br>GCAGACCCCCACGGACGCGCCAGCTCCGCCGCGCTCGCTGACAGCCCCGC | (SEQ ID NO: 43) |
| >chr13: 25745729-25745779<br>CGCCGCCGCGGCTCCGGCTCGTCTCCATGGAAACCGCGCGGGATAAGCCG | (SEQ ID NO: 44) |
| >chr13: 112723513-112723563<br>GCTCACTTTCCTCCGCGTTGCTTCCGGACGGCGCCGACCGCCGGAGCCCA | (SEQ ID NO: 45) |
| >chr13: 93879295-93879345<br>CGGCGCGCGCTCCCACCTTTGCCGCACACTCCGGCGAGCCGAGCCCGCAG | (SEQ ID NO: 46) |
| >chr13: 110960091-110960141<br>CCCTGCATGCGGGCCGCGCACCGCGCTGTCCCCGCGTCTCGCGGACCGAG | (SEQ ID NO: 47) |

TABLE 1-continued

Examples of Sequences of Particular MRs

| METHYLATABLE REGION | SEQUENCE IDENTIFIER |
|---|---|
| >chr13: 110960291-110960341<br>GCGGTAAGCGACTTTCTGCCTGGTCCCCGTGGGTCACGCGCGCATGGACC | (SEQ ID NO: 48) |
| >chr14: 102030638-102030688<br>CCCCGCCCTCACTGTCTCGCCTGTTGCGCCCGGAGTGAGGGCGACCCGGG | (SEQ ID NO: 49) |
| >chr14: 24780706-24780756<br>CAGTTCTAGCGTCAACCCGGTGCTCTACGTCTTCACCGCTGGAGATCTGC | (SEQ ID NO: 50) |
| >chr14: 36986567-36986617<br>ACCTGGCCCTGCAGCGCCGCGGGGCTGGCGGCGTGGTGCGCCAGGTCCGG | (SEQ ID NO: 51) |
| >chr14: 102030634-102030684<br>CAATCCCCGCCCTCACTGTCTCGCCTGTTGCGCCCGGAGTGAGGGCGACC | (SEQ ID NO: 52) |
| >chr16: 1843738-1843788<br>TGCGGGGCAGCCCGCGCCTGTCACCTGGCTGGCCCAACCCAGCTGGCCCT | (SEQ ID NO: 53) |
| >chr16: 67197630-67197680<br>GACGCCTTCCGCGCGCACTGCCCGCGCCTGCGCACCTATACCCTCAAGCT | (SEQ ID NO: 54) |
| >chr16: 67199230-67199280<br>ACTGTGGTCGCTCCAGGCTAGGCCTCGGAGCCCGTTCTGGCCTGGCCTCG | (SEQ ID NO: 55) |
| >chr16: 67197638-67197688<br>CCGCGCGCACTGCCCGCGCCTGCGCACCTATACCCTCAAGCTCACGCGCG | (SEQ ID NO: 56) |
| >chr16: 67199238-67199288<br>CGCTCCAGGCTAGGCCTCGGAGCCCGTTCTGGCCTGGCCTCGACCCATAT | (SEQ ID NO: 57) |
| >chr16: 67197634-67197684<br>CCTTCCGCGCGCACTGCCCGCGCCTGCGCACCTATACCCTCAAGCTCACG | (SEQ ID NO: 58) |
| >chr16: 67197684-67197734<br>CGCGAGCCGCATCCCTGGAGGCCTACGCTCGTGGCGTGATTGGGCGACTT | (SEQ ID NO: 59) |
| >chr16: 67199234-67199284<br>TGGTCGCTCCAGGCTAGGCCTCGGAGCCCGTTCTGGCCTGGCCTCGACCC | (SEQ ID NO: 60) |
| >chr16: 67197607-67197657<br>GCGTGGTGAGCCACTCGGTGCTGGACGCCTTCCGCGCGCACTGCCCGCGC | (SEQ ID NO: 61) |
| >chr16: 67199257-67199307<br>GAGCCCGTTCTGGCCTGGCCTCGACCCATATCCCCGTAAGCGGCAGGCCT | (SEQ ID NO: 62) |
| >chr16: 58019089-58019139<br>GAGGGGCTTTCTGTTCGCAGCGGAGGGTCTCAGCGGCTACGCGGTGCGGT | (SEQ ID NO: 63) |
| >chr16: 10480062-10480112<br>GCCGGCCCCGGAGGCCTCGGAGCGCCGGGCCTACCGGACGTTTGCGGCGA | (SEQ ID NO: 64) |
| >chr16: 2287567-2287617<br>ACGCGGCGCCGCATCAAGCCGTGGCGGAGATCGACGCGCTCTACGACGTG | (SEQ ID NO: 65) |
| >chr16: 86613474-86613524<br>GCCTGTGGGTTCAGGGAAGTGTTACCAACCATTGCGCGCAGGTGGGCGCG | (SEQ ID NO: 66) |
| >chr16: 67197644-67197694<br>GCACTGCCCGCGCCTGCGCACCTATACCCTCAAGCTCACGCGCGAGCCGC | (SEQ ID NO: 67) |
| >chr17: 3792137-3792187<br>CGCGTGTGTGAGGGCGTGTGTCCCCACAGGAGGGAATATGTGTGCGCAGG | (SEQ ID NO: 68) |
| >chr17: 42431530-42431580<br>GCGTCGGTGCTGCGTGCCCCGCCGCCCGCCTGCAGGTCGATGTAAGAGTG | (SEQ ID NO: 69) |
| >chr17: 46620639-46620689<br>GGGCTCCAGCCCGCCGGCCCCGCGCAGCGCGCAGCCGGGACTCGACGCGC | (SEQ ID NO: 70) |
| >chr17: 42431515-42431565<br>CCCGAGTCCAGGCTGGCGTCGGTGCTGCGTGCCCCGCCGCCCGCCTGCAG | (SEQ ID NO: 71) |
| >chr17: 46620633-46620683<br>TGGCCCGGGCTCCAGCCCGCCGGCCCCGCGCAGCGCGCAGCCGGGACTCG | (SEQ ID NO: 72) |

TABLE 1-continued

Examples of Sequences of Particular MRs

| METHYLATABLE REGION | SEQUENCE IDENTIFIER |
|---|---|
| >chr17: 8129970-8130020<br>atttctagtccatcgccttaaccactcggccacgactacGAGGCTTAGGG | (SEQ ID NO: 73) |
| >chr17: 8013162-8013212<br>GGCTTGGGGCGGGTAGCGGGGCAAAGCGTCTTCGGGGGCGGAGATCAGT | (SEQ ID NO: 74) |
| >chr17: 74072963-74073013<br>ACCTACGCGCGCACCTTGCGCTACCTCTGGCGCGCCGTCGACCCGGTGGC | (SEQ ID NO: 75) |
| >chr17: 59482512-59482562<br>TCGTCGGCCTCCGCCCAGGCCCCTGTAATCCGCGCGCCCTCTCCCCGCAG | (SEQ ID NO: 76) |
| >chr19: 40729345-40729395<br>GCCGGGGTGGTGCAGCCGGAAATCCAGGCGGCTCAGGATGCGACGCTCGG | (SEQ ID NO: 77) |
| >chr19: 55598629-55598679<br>CCGCCGACCGGCCTGACCGCGCCCGGGCTGCCCTCGCTCAGGACCGTGGA | (SEQ ID NO: 78) |
| >chr19: 10207315-10207365<br>CGCGGGGATGCGCGCGTCTACACCCGCGATGTCCCGGGCCCATAATTTCA | (SEQ ID NO: 79) |
| >chr19: 10207308-10207358<br>GCTTCCACGCGGGGATGCGCGCGTCTACACCCGCGATGTCCCGGGCCCAT | (SEQ ID NO: 80) |
| >chr19: 40723212-40723262<br>AGTACCTTGAGACAGTACTCGCGCACGCGCTCGTAGTTTACCAGCTCCGA | (SEQ ID NO: 81) |
| >chr19: 58570407-58570457<br>ACACGAAAGCCCGTGTGGTCGCGCCGGGAGCTCACGGCGTTCCAAGCGGC | (SEQ ID NO: 82) |
| >chr19: 38886701-38886751<br>gcgccctgcgcgcgtgccactgggtcgcagcgcgatgcggctgcgccgg | (SEQ ID NO: 83) |
| >chr19: 45655611-45655661<br>GGAAAACGTCCCAGAggcgcgcgcggccctcgggcgcgccccggTCTGC | (SEQ ID NO: 84) |
| >chr19: 2291486-2291536<br>CGCCGGGCTCCACGTGCGCGATGGCGTTCTCGCTCAGGTCCAGCTCCTCC | (SEQ ID NO: 85) |
| >chr19: 2291536-2291586<br>AGCGCGGGCAGCGCGGCCAGGTCGCCCGGGTTCAGGCAGCGGATGCGGTT | (SEQ ID NO: 86) |
| >chr19: 38886711-38886761<br>gcgcgtgccactgggtcgcagcgcgatgcggctgcgccggctgcgGGGGT | (SEQ ID NO: 87) |
| >chr19: 2291483-2291533<br>AGGCGCCGGGCTCCACGTGCGCGATGGCGTTCTCGCTCAGGTCCAGCTCC | (SEQ ID NO: 88) |
| >chr19: 2291533-2291583<br>TCCAGCGCGGGCAGCGCGGCCAGGTCGCCCGGGTTCAGGCAGCGGATGCG | (SEQ ID NO: 89) |
| >chr19: 51162202-51162252<br>GGTGGCTCATCGCGGTCACGGACTTCCAGACGCGCTCGCGCTTGCTGCGC | (SEQ ID NO: 90) |
| >chr19: 10207299-10207349<br>GACCCCTCCGCTTCCACGCGGGGATGCGCGCGTCTACACCCGCGATGTCC | (SEQ ID NO: 91) |
| >chr1: 16266159-16266209<br>TCGCAGACACCGGGGCTGGGTTTCTCTTTCCTCTTTTTGGAGAAAAGGAA | (SEQ ID NO: 92) |
| >chr1: 26487912-26487962<br>GTGGGAGTCCTGGGCCGCTCACGCCGCACCCCTGCAACGAGCTGGGGCCC | (SEQ ID NO: 93) |
| >chr1: 27677813-27677863<br>CGCCGGCTCCGAGGGTGAGTGACAGCCGGAGAGGCCAAGCTGGACACGCC | (SEQ ID NO: 94) |
| >chr1: 91172178-91172228<br>GGTACGCGCCGAGCAAGAACCCGCACGGAGCCGGCGCGCCGCGGCTGGGC | (SEQ ID NO: 95) |
| >chr1: 204328922-204328972<br>CCCTGGGGCCCCTTCTGCAGAGCGGGGCTCCGGATCTAATCTGATCTAA | (SEQ ID NO: 96) |
| >chr1: 200842333-200842383<br>AACGCCTTTGTGGTGTGGCTGCTggccgggcggcggggcccgcggcggcT | (SEQ ID NO: 97) |

TABLE 1-continued

Examples of Sequences of Particular MRs

| METHYLATABLE REGION | SEQUENCE IDENTIFIER |
|---|---|
| >chr1: 247611505-247611555<br>CATCTTGGTCTCGGCGGCGGCGACGGCGGCGAGGACGCGGAGCACTCTGG | (SEQ ID NO: 98) |
| >chr1: 47899139-47899189<br>TGGCGCTGTTTTCGGTCTCTCCTGAGGTCGCAACCCTCTTCCCACGAACA | (SEQ ID NO: 99) |
| >chr1: 47905389-47905439<br>GTCTCCAGACCTTGGGCCGGCACGCGTGACACGGCACTTCAGGCTCCACG | (SEQ ID NO: 100) |
| >chr1: 4715392-4715442<br>ACCGGCGCCGCGGGACGGAAGCGAGCGGGCGCGGGCGCCGCGCAGATGGC | (SEQ ID NO: 101) |
| >chr1: 26487911-26487961<br>CGTGGGAGTCCTGGGCCGCTCACGCCGCACCCCTGCAACGAGCTGGGGCC | (SEQ ID NO: 102) |
| >chr1: 201088573-201088623<br>gattgatgaaattcgcatcccgacccacgggtgtcgaagtcatcacttc | (SEQ ID NO: 103) |
| >chr20: 37354855-37354905<br>CGGCGTCCCTGGAGCGCACTATCACTGGGGCCACGGAAGGCAGGTTTTCT | (SEQ ID NO: 104) |
| >chr20: 57225128-57225178<br>CACACACGTGTGTAAAGTTTGTTCCACGCAGAAACAAAGGACGCGTGGGG | (SEQ ID NO: 105) |
| >chr20: 61637181-61637231<br>GGCGCAGAGTCCAGCGTCCGGCTCTCGAGCTCAATCCCGCGCCCCGACGG | (SEQ ID NO: 106) |
| >chr20: 61637381-61637431<br>GGGCCGGGGGCCCGCGCGGTCACGGCTTCTCGTGACAGTGTTTGCAAAGC | (SEQ ID NO: 107) |
| >chr20: 61637431-61637481<br>GCGGAGGGCGTCCCGGAGAAGGCGGCGCACTTGTCAGGGCAGGGCCCCAG | (SEQ ID NO: 108) |
| >chr20: 21687147-21687197<br>GCTTGCGCATTGTGGAGCTGGCGCAGCTGGGCATCCGACCCTGTGACATC | (SEQ ID NO: 109) |
| >chr20: 21503099-21503149<br>CATCGCCACCGCCGGGCTCCGCTGCGGCTCCCGGGCTCCGCCGGGTGCCC | (SEQ ID NO: 110) |
| >chr20: 32255840-32255890<br>GACAAGGAGCTGGAGGCGCAGTGCCGGCGGCACGGCTACGCGGCCCTGCG | (SEQ ID NO: 111) |
| >chr20: 32255854-32255904<br>GGCGCAGTGCCGGCGGCACGGCTACGCGGCCCTGCGGCCCCACCTGGTGG | (SEQ ID NO: 112) |
| >chr20: 62679512-62679562<br>GGCGGCCTAGCCGGAGATGCACGCGCTGTAATAGACCGCGCTGCTGGCGT | (SEQ ID NO: 113) |
| >chr22: 21386720-21386770<br>GCTCCGCCGCGCCCCCGTCCCCGGACACCTGCGCCTTCGCCTGTTCTTGG | (SEQ ID NO: 114) |
| >chr2: 42720509-42720559<br>CTCGGAGCGGCAGCCGTGCAGCCGGCTCACGCGGCGCAGCGGGAAGTCCT | (SEQ ID NO: 115) |
| >chr2: 63275792-63275842<br>GCGCCGGGCTATGGACGCGGACGCCGGCGAAGCGCACCCCGGGACGTCCG | (SEQ ID NO: 116) |
| >chr2: 45170002-45170052<br>TTTAAGAACCGGCGGCAGCGCGACCGCGCCGCGGCGGCCAAGAACAGGTT | (SEQ ID NO: 117) |
| >chr2: 20870374-20870424<br>GCTGTCCACGTGCCCGGGCGCCGCCCGAGCGCCACGCCTGCTGTACTCGC | (SEQ ID NO: 118) |
| >chr2: 20871024-20871074<br>TTCAGACGCTGCTCAACTCCATGGCACCAGACGCGGCGCCGGCCTCCTGC | (SEQ ID NO: 119) |
| >chr2: 209271556-209271606<br>GCGCCGCGGCGCAGCAGCACGCGGGTTCTGAGAAGCGCGTGGCTCCGGCG | (SEQ ID NO: 120) |
| >chr2: 182547907-182547957<br>AAATTTCGACCCGGGGCGCCGGCATCGCGACGCTCAGCCAGTGCCCGCGA | (SEQ ID NO: 121) |
| >chr2: 149633319-149633369<br>GCTGGGGCGTCTGCCTTCCCTGCTGCTCCGCGCCGCAGCTGGGCGCCCCG | (SEQ ID NO: 122) |

TABLE 1-continued

Examples of Sequences of Particular MRs

| METHYLATABLE REGION | SEQUENCE IDENTIFIER |
|---|---|
| >chr2: 42720477-42720527<br>TCGTAGTCGTCGCACACCTCGAGCACGTCGCGCTCGGAGCGGCAGCCGTG | (SEQ ID NO: 123) |
| >chr2: 42720527-42720577<br>CAGCCGGCTCACGCGGCGCAGCGGGAAGTCCTTCAGCAGCTCCCGGGACA | (SEQ ID NO: 124) |
| >chr2: 233350678-233350728<br>TGAGGTCCCATCGCGCCGCGACCCCCGGACGCTCCTCCGCGCCGCCCAGG | (SEQ ID NO: 125) |
| >chr2: 5837049-5837099<br>GGGGCTCCGGCGGCGGCGCGGGCGCGACCCATCCCGCTGGCGCTCCCCGC | (SEQ ID NO: 126) |
| >chr2: 27988834-27988884<br>AGTGTCGCGTGGCTGGCAATCCGCGGCGGCCTCCGGCGCATGCGCAGTTC | (SEQ ID NO: 127) |
| >chr2: 39187664-39187714<br>CCGAgcgcgccgcgcaggcgcacggcccggccgccgccgccgtcgccgcc | (SEQ ID NO: 128) |
| >chr3: 61549435-61549485<br>CGTCGTGCGACCCGGAGCAGGGCGCGCGGGAGCCCTCGTCGCCCTTGGGG | (SEQ ID NO: 129) |
| >chr3: 147102832-147102882<br>ACACCTGCGCGTCTCTCGCGCGCCGGGATCCTTTCTCCCAACGTTTTACC | (SEQ ID NO: 130) |
| >chr3: 195934241-195934291<br>AAGCTGACCACCCGCGGCCCCGCGTACCTTGCCCTTGTAGGTGCGGTCGG | (SEQ ID NO: 131) |
| >chr3: 142839123-142839173<br>CGTCGCTGGAGCCGGGAGGCGCCGGGTTCGGCGGAGCGCGGAGCGGGCT | (SEQ ID NO: 132) |
| >chr4: 5890055-5890105<br>CTCTCGGCCCCGCTCCCAGCGGGCGCGCTGACAAAGGCCCGGGAGGGATA | (SEQ ID NO: 133) |
| >chr4: 13545573-13545623<br>TGAGACGCTGGCGGACATCTCGCTGTCGCTCCGGCCCGCGGCTTCCTCCT | (SEQ ID NO: 134) |
| >chr4: 111542356-111542406<br>ATTTCTTCGCGTGTGGACATGTCCGGGTAGCGGTTCCTCTGGAAAGTGGC | (SEQ ID NO: 135) |
| >chr5: 44389810-44389860<br>CTGCTAAAGCGTCCTATGCTTGCAGCGCGGGCCACGGCGCTGACGGTATC | (SEQ ID NO: 136) |
| >chr5: 37837026-37837076<br>CTCCCCGCGTCGCCAGAGGAGGCTCCCGGCTGCGGTTCCCGCCCTCGGCC | (SEQ ID NO: 137) |
| >chr5: 138729767-138729817<br>GCGGCTCCGTCCCGGGCGCAGGCTTGTCGCGCCGAATCGCGCGCTCGCGG | (SEQ ID NO: 138) |
| >chr5: 138729769-138729819<br>GGCTCCGTCCCGGGCGCAGGCTTGTCGCGCCGAATCGCGCGCTCGCGGAG | (SEQ ID NO: 139) |
| >chr5: 2756979-2757029<br>AGACACGCGCGCGCTCGCGCTTCCCGGAGAGGTCGGCGCGTCTCGCTGAA | (SEQ ID NO: 140) |
| >chr5: 2756095-2756145<br>ATCCCCGAGTAGCCACGCGGGCGCCACTTCAGGGACGCGGGGCGGCGGCT | (SEQ ID NO: 141) |
| >chr5: 2756945-2756995<br>CGCGCACGGCAGGCCCAGATCCGCACAGAGACGCAGACACGCGCGCGCTC | (SEQ ID NO: 142) |
| >chr5: 138729785-138729835<br>CAGGCTTGTCGCGCCGAATCGCGCGCTCGCGGAGGCTGGGCCACGGCCTC | (SEQ ID NO: 143) |
| >chr5: 140864580-140864630<br>CACCAGCAAAAACGGCGCGTAACCCTTGCGGCGCCGGCCGAACCGCGCCA | (SEQ ID NO: 144) |
| >chr5: 140864591-140864641<br>ACGGCGCGTAACCCTTGCGGCGCCGGCCGAACCGCGCCAGAGCTGGCGCG | (SEQ ID NO: 145) |
| >chr6: 108883038-108883088<br>ACCCACCCCGGGCTGGCAGCAGGACCCGCCGGGCCTCCTGCGCAGCGCGA | (SEQ ID NO: 146) |
| >chr6: 27107296-27107346<br>CGTGACCTACACGGAGCACGCCAAGCGCAAGACGGTCACCGCCATGGACG | (SEQ ID NO: 147) |

TABLE 1-continued

Examples of Sequences of Particular MRs

| METHYLATABLE REGION | SEQUENCE IDENTIFIER |
|---|---|
| >chr6: 393339-393389<br>ACCGCGAGGAGGACGCCGCGCTCTTCAAGGTCTCCGGCCTCGGGAgccgg | (SEQ ID NO: 148) |
| >chr6: 166580824-166580874<br>CCCAGGCGCTGGAGAGCGCGGCGCGCGGGCTCCGGACGCGCACCCACC | (SEQ ID NO: 149) |
| >chr6: 166581374-166581424<br>GCCGCGGCGGCAGCGCTGGGGTGCTCGGCGGATTGGGCCGCGCACGCTTT | (SEQ ID NO: 150) |
| >chr6: 27107311-27107361<br>GCACGCCAAGCGCAAGACGGTCACCGCCATGGACGTGGTCTACGCGCTCA | (SEQ ID NO: 151) |
| >chr6: 27107282-27107332<br>GTGATCCGGGACGCCGTGACCTACACGGAGCACGCCAAGCGCAAGACGGT | (SEQ ID NO: 152) |
| >chr6: 27107332-27107382<br>CACCGCCATGGACGTGGTCTACGCGCTCAAGCGCCAGGGCCGCACCCTCT | (SEQ ID NO: 153) |
| >chr6: 27107288-27107338<br>CGGGACGCCGTGACCTACACGGAGCACGCCAAGCGCAAGACGGTCACCGC | (SEQ ID NO: 154) |
| >chr6: 27107326-27107376<br>GACGGTCACCGCCATGGACGTGGTCTACGCGCTCAAGCGCCAGGGCCGCA | (SEQ ID NO: 155) |
| >chr7: 100463660-100463710<br>TGGCCCCTCAACCTGCTGCGGCCCCGGGGTGGGCCCGGCTATGTGGATGT | (SEQ ID NO: 156) |
| >chr7: 27154894-27154944<br>GGCAAGATTTATGACTCGGCGCCCCAAAGCTGTAAACAGAGCACAAAACA | (SEQ ID NO: 157) |
| >chr7: 150038925-150038975<br>GCCGCGGCTGCAGGCGGCTCGCCCAGGCGCGCAGCCCTCGGTCCCACCTC | (SEQ ID NO: 158) |
| >chr7: 19156544-19156594<br>TCTTCCGCAGCGCGGCGAACGCCTCGTTCAGCGACTGGGTGCGCTGGCGC | (SEQ ID NO: 159) |
| >chr7: 90895183-90895233<br>GCTGCGCCTCCACGCTCTTCACGGTGCTTACGTACCTGGTGGACATGCGG | (SEQ ID NO: 160) |
| >chr7: 155597687-155597737<br>GAGTCGTCGAGTCGCACGGCCCGGCTTGACACGCTGCGCCCCGCGCCCCC | (SEQ ID NO: 161) |
| >chr7: 150778962-150779012<br>CTGTTCCCGGCCGGGAAACTGGGTCCTGAGGAGAGAGGGACCTGGGTAAG | (SEQ ID NO: 162) |
| >chr7: 54609918-54609968<br>CGCCCTccgcggccgcccggcgcgagctcccgggcggggcgcTGTCCAGC | (SEQ ID NO: 163) |
| >chr7: 64030153-64030203<br>GTGATGGTCGGAGGATAGTTGACTGTGACCAGCACGCGGCGGCTGTCGGG | (SEQ ID NO: 164) |
| >chr7: 64030203-64030253<br>CGCCGAGTTAACCCCGTTGTGAGTCACGCACTCATACTCCCCGGCCTGGC | (SEQ ID NO: 165) |
| >chr7: 64030553-64030603<br>GCAGCCGCACCCGCGGGTCCCTGGTCCTGCGGTCGTTGCCGGCGTACAGG | (SEQ ID NO: 166) |
| >chr8: 10589506-10589556<br>CCGCGCGCAGCGACCGATGCCTTGCATGCAACATGCAACGGGCCCGACGG | (SEQ ID NO: 167) |
| >chr8: 104513726-104513776<br>GCAGGGGATGCGGACGCCACCCTGGTCCCACGCCTCCGCGGGGCGGCTCT | (SEQ ID NO: 168) |
| >chr8: 37557219-37557269<br>TGGGGTAGGTGACTCTCGCTAGATCCCTCCAAAGCAGACCGGTGGCGATG | (SEQ ID NO: 169) |
| >chr9: 127267427-127267477<br>CCGGCTCCCCGGACCCCGAGCGCGGCCAGAGAGCTGCGGAGCCCGAGTGC | (SEQ ID NO: 170) |
| >chr9: 124988397-124988447<br>AGAGACGATACCGAAACCCAATGGACCGCGAGGACCGAAGGCAGATCCGG | (SEQ ID NO: 171) |
| >chr9: 124988497-124988547<br>GCCGCTGAGCGCCGGCAGGTTGGACCAGCGCTGCGCGCCGGAAGTGCACT | (SEQ ID NO: 172) |

TABLE 1-continued

Examples of Sequences of Particular MRs

| METHYLATABLE REGION | SEQUENCE IDENTIFIER |
|---|---|
| >chrX: 152599863-152599913<br>ATGTGCAGGGGGTGCAGGACTGTGTGCGGGGCTGGAGCGAGTGTGCGGGC | (SEQ ID NO: 173) |
| >chrX: 77359521-77359571<br>TTGCGGTTCGCGGCGTGCCGGACGTGACAAACGGAAGCCGCACGTCTCAC | (SEQ ID NO: 174) |
| >chrX: 47078882-47078932<br>GGCGGGGTGCGGAGCGGGTGAGGGACCCGAGGGTGTATAACGGGGGGTAG | (SEQ ID NO: 175) |
| >chrX: 136651251-136651301<br>GGTTTGTAAACACTCGGCCCGACGCCGGGCCGCGGAACGGAAGCGCCCGC | (SEQ ID NO: 176) |

In methods for assaying the methylation level of one or more MRs encompassed herein, the methods may comprise obtaining a sample from an individual that comprises the genomic DNA to be assayed. In some embodiments, one entity obtains the sample from the individual whereas a different entity performs the assaying, although in some cases obtaining of the sample and assaying the sample are performed by the same entity.

III. Individuals for Screening and Samples Thereof

An individual, typically a human individual, subjected to methods and compositions of the disclosure may be of any kind, so long as it is desired to know whether or not the individual has or is at risk for having or is in need of prognosis, response to treatment, typing and/or staging of CRC. In some embodiments, the individual is a human at least 40, 50, 55, 60, 65, or 70 years or older in age, although in some cases less than 50 years old and may or may not have family or personal history and/or symptoms of CRC. In some embodiments, this individual is less than 50 years old and has a personal or family history of any type of cancer, including CRC. The individual may have one or more symptoms of CRC or may be asymptomatic for CRC. In some cases, the individual has a prior history of having cancer, including a prior history of having CRC.

In cases wherein an individual has one or more symptoms of a colorectal medical disorder, the individual may be subjected to methods and/or compositions of the disclosure. In specific cases, the individual has one or more symptoms selected from the group consisting of a change in bowel habits, constipation that lasts more than a couple of weeks, diarrhea that lasts more than a couple of weeks, a feeling that the bowel does not empty completely, blood in the stool, narrow or thinner than normal stool, abdominal discomfort, gas pains, bloating, fullness, cramps, weight loss, fatigue, anemia, and a combination thereof.

A person who is at risk for developing CRC may be an individual over 50 years in age and/or with a personal or family history of CRC and/or has or has had colon polyps, and/or is positive for hemoccult test and/or had surgery for CRC and/or has low fiber diet and/or high fat diet and/or is a tobacco user and/or suffered from inflammatory bowel disease(s). In cases where the individual has had a person or family history, the individual may have a personal or family history of familial adenomatous polyposis, Lynch syndrome, Peutz-Jeghers syndrome or juvenile polyposis syndrome, for example.

In some cases of the disclosure, the individual is subjected to one or more other assays for determination of CRC in addition to the methods and/or compositions of the disclosure. Although any other assay may be employed, in some cases the one or more other assays is selected from the group consisting of stool testing, barium enema, virtual colonoscopy, sigmoidoscopy, carcinoembryonic antigen (CEA) tests, KRAS tests, microsatellites deficiency tests, colonoscopy, a combination thereof, etc. The other one or more assays besides the method of the present disclosure that may be used can be employed for an individual to identify whether or not there are polyps in the colon of the individual, and cancer may be identified at that time.

In cases where the individual has been identified as having CRC, this condition may originate in the colon or rectum of the individual (or may be a primary cancer that metastasizes to the colon and/or rectum). In some cases, when the individual is determined to have cancer, the individual has CRC in stage 0, 1, 2, 3, or 4.

Any type of CRC may be encompassed with methods and compositions of the invention, including polyps, adenoma less than 1 cm, adenoma more than 1 cm, adenocarcinomas, and also all microsatellites-proficient and microsatellites-deficient cancer types.

IV. Measuring Methylation Level

In embodiments of the disclosure, the methylation level of one or more MRs is determined, including for diagnosing, screening, and/or prognosing CRC in an individual. In particular aspects of the disclosure, the methylation level measurements are quantifiable. The methylation may be determined over the sequence overlapping an MR. The actual locations of these MRs are provided. The corresponding sequences are also included herewith, although a skilled artisan can obtain them from the MRs locations from public databases such as the National Center for Biotechnology Information's database (ENTREZ), the EMBL Nucleotide Sequence Database (also known as EMBL-Bank) and the UCSC Genome Browser.

The methylation level can be determined by any suitable means in the art, although in specific embodiments the methylation level is determined with methylation-specific PCR (including probe-based real-time PCR for methylation analysis; see, for example, Herman et al., 1996; Goel et al., 2004; Ishiguro et al., 2006) (such as methylight PCR (Qiagen; Valencia, Calif., Applied Biosystems, Roche Diagnostics)); methylation array (Illumina, Agilent, Affymetrix); methylation sequencing (including bisulfite DNA sequencing; see Ballot et al., 2003; and Oster et al., 2011; Kim et al., 2011, for example); methyl-beaming (Nature Biotechnol. 2009, September; 27(9): 858-863 for example); mass spectrometry; a combination thereof; and so forth. In some methods, quantity of DNA is required for comparison, and there are standard means in the art for identifying DNA quantity, including spectrophotometry and/or gel electrophoresis, for example. Thus, numerous methods for analyzing methylation levels of an MR are known in the art and can be used in the methods of the present invention to identify methylation level of an MR.

In specific embodiments, part of the analysis of methylation includes bisulfite genomic sequencing, whether by Sanger or NGS sequencing or any other technology. Accordingly, denatured genomic DNA can be treated with freshly prepared bisulfite solution at 55° C. in the dark overnight (or only incubation for 3 hours), followed by column purification and NaOH treatment, for example. Bisulfite treatment modifies DNA converting un-methylated, but not methylated, cytosines to uracil (Chatterjee et al. Nucleic Acids Res. 2012 May; 40(10): e79. doi: 10.1093/nar/gks150. Epub 2012 Feb. 16.)

In some embodiments, methylation assays allow for determination of the methylation state of one or a plurality of CpG dinucleotides within a DNA sequence. Such assays involve, among other techniques, DNA sequencing of bisulfite-treated DNA, PCR (for sequence-specific amplification), Southern blot analysis, use of methylation-sensitive restriction enzymes, etc. For example, genomic sequencing has been simplified for analysis of DNA methylation patterns and 5-methylcytosine distribution by using bisulfite treatment (Frommer et al., Proc. Natl. Acad. Sci. USA 89:1827-1831, 1992). Additionally, restriction enzyme digestion of PCR products amplified from bisulfite-converted DNA is used, e.g., the method described by Sadri and Homsby (Nucl. Acids Res. 24:5058-5059, 1996), or Combined Bisulfite Restriction Analysis (COBRA) (Xiong and Laird, Nucleic Acids Res. 25:2532-2534, 1997).

Combinations of multiple methods for quantifying methylation may be employed.

A. COBRA

COBRA analysis is a quantitative methylation assay useful for determining DNA methylation levels at specific genomic loci in small amounts of genomic DNA (Xiong and Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the interested MRs, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from micro-dissected paraffin-embedded tissue samples or body fluids circulating DNA. Typical reagents (e.g., as might be found in a typical COBRA-based kit) for COBRA analysis may include, but are not limited to: PCR primers for specific MR (or methylation-altered DNA sequence or CpG island); restriction enzyme and appropriate buffer; gene-hybridization oligo; control hybridization oligo; kinase labeling kit for oligo probe; and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

B. MethyLight

The MethyLight assay is a high-throughput quantitative methylation assay that utilizes fluorescence-based real-time PCR (TaqMan®) technology that requires no further manipulations after the PCR step (Eads et al., Cancer Res. 59:2302-2306, 1999). Briefly, the MethyLight process begins with a mixed sample of genomic DNA that is converted in a sodium bisulfite reaction to a mixed pool of methylation-dependent sequence differences according to standard procedures (the bisulfite process converts un-methylated cytosine residues to uracil). Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both.

The MethyLight assay may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique), or with oligonucleotides covering potential methylation sites.

The MethyLight process can be used with a "TaqMan®" probe in the amplification process. For example, double-stranded genomic DNA is treated with sodium bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10° C., higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight-based kit) for MethyLight analysis may include, but are not limited to: PCR primers for specific MR (or methylation-altered DNA sequence or CpG island); TaqMan® probes; optimized PCR buffers and deoxynucleotides; and Taq polymerase.

C. Ms-SNuPE

The Ms-SNuPE technique is a quantitative method for assessing methylation differences at specific CpG sites based on bisulfite treatment of DNA, followed by single-nucleotide primer extension (Gonzalgo and Jones, Nucleic Acids Res. 25:2529-2531, 1997). Briefly, genomic DNA is reacted with sodium bisulfite to convert un-methylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., microdissected pathology sections), and it avoids utilization of restriction enzymes for determining the methylation level at CpG sites. Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

D. Methylated CpG Island Amplification (MCA)

The MCA technique is a method that can be used to screen for altered methylation patterns in genomic DNA, and to isolate specific sequences associated with these changes (Toyota et al., Cancer Res. 59:2307-12, 1999). Briefly, restriction enzymes with different sensitivities to cytosine methylation in their recognition sites are used to digest genomic DNAs from primary tumors, and normal tissues prior to arbitrarily primed PCR amplification. Fragments that show differential methylation are cloned and sequenced after resolving the PCR products on high-resolution polyacrylamide gels. The cloned fragments are then used as probes for Southern analysis to confirm differential methylation of these regions. Typical reagents (e.g., as might be found in a typical MCA-based kit) for MCA analysis may include, but are not limited to: PCR primers for arbitrary priming Genomic DNA; PCR buffers and nucleotides, restriction enzymes and appropriate buffers; gene-hybridization oligos or probes; control hybridization oligos or probes.

E. Methyl-BEAMing:

In BEAMing, PCR amplification of individual DNA molecules takes place within aqueous nano-compartments suspended in a continuous oil phase. Each aqueous nano-compartment contains the DNA polymerase, cofactors, and dNTPs required for PCR. When a compartment contains a single DNA template molecule as well as a bead, the PCR product within the compartment becomes bound to the bead. Each bead thereby ends up with thousands of identical copies of the template within its nano-compartment a process similar to that resulting from cloning an individual DNA fragment into a plasmid vector to form a bacterial colony. After PCR, the beads are collected by breaking the emulsion and their status is individually assessed by incubation with fluorescent hybridization probes. In Methyl-BEAMing, the status of harvested beads is interrogated by fluorescent probes that specifically hybridize to either methylated or un-methylated derived sequences, with flow-cytometry providing an accurate enumeration of the fraction of original template molecules that were methylated or un-methylated within the queried sequence (Li et al., Nature Biotechnology 2009 September; 27(9):858-863).

F. Methylation Specific Polymerase Chain Reaction (MSP)

One embodiment provides a method for detecting a methylated CpG-containing nucleic acid, the method including contacting a nucleic acid-containing specimen with an agent that modifies un-methylated cytosine; amplifying the CpG-containing nucleic acid in the specimen by means of CpG-specific oligonucleotide primers; and detecting the methylated nucleic acid. It is understood that while the amplification step is optional, it is desirable in the preferred method.

The term "modifies"—as used herein—refers to the conversion of an un-methylated cytosine to another nucleotide that will distinguish the un-methylated from the methylated cytosine. Preferably, the agent modifies un-methylated cytosine to uracil. Preferably, the agent used for modifying un-methylated cytosine is sodium bisulfite, however, other agents that similarly modify un-methylated cytosine, but not methylated cytosine can also be used in the method of the invention or any method allowing the distinguishing between the methylated cytosine and the un-methylated cytosine. Sodium bisulfite ($NaHSO_3$) reacts readily with the 5,6-double bond of cytosine, but poorly with methylated cytosine. Cytosine reacts with the bisulfite ion to form a sulfonated cytosine reaction intermediate that is susceptible to deamination, giving rise to a sulfonated uracil. The sulfonate group can be removed under alkaline conditions, resulting in the formation of uracil. Uracil is recognized as a thymine by Taq polymerase and therefore upon PCR, the resultant product contains cytosine only at the position where 5-methylcytosine occurs in the starting template DNA.

Some primers used in the disclosure for amplification of the CpG-containing nucleic acid in the specimen, after bisulfite modification, specifically distinguish between methylated and non-methylated DNA, in particular embodiments of the disclosure. Two exemplary types of primers could be designed: one set recognizing methylated cytosine and the other set targeting the un-methylated cytosine. The first set of primers enables one to assess the methylation; however, the second set enables one to quantify the un-methylated DNA. MSP primers for the non-methylated DNA preferably have a T in the 3' CG pair to distinguish it from the C retained in methylated DNA, and the complement is designed for the antisense primer. MSP primers usually contain relatively few Cs or Gs in the sequence since the Cs will be absent in the sense primer and the Gs absent in the antisense primer (C becomes modified to U (uracil) which is amplified as T (thymidine) in the amplification product).

The primers of the disclosure embrace oligonucleotides of sufficient length and appropriate sequence so as to provide specific initiation of polymerization on a significant number of nucleic acids in the polymorphic locus. Specifically, the term "primer" as used herein refers to a sequence containing two or more deoxyribonucleotides or ribonucleotides, in certain cases more than three, and in particular cases more than 8, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. In particular cases, the primer is an oligodeoxy ribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

Primers of the disclosure are designed to be "substantially" complementary to each strand of the genomic locus to be amplified and include the appropriate G or C nucleotides as discussed above. This means that the primers must be sufficiently complementary to hybridize with their respective strands under conditions that allow the agent for polymerization to perform. In other words, the primers should have sufficient complementarity with the 5' and 3' flanking sequences to hybridize therewith and permit amplification of the genomic locus.

Oligonucleotide primers of the disclosure are employed in the amplification process that is an enzymatic chain reaction that produces exponential quantities of target locus relative to the number of reaction steps involved. Typically, one primer is complementary to the negative (−) strand of the locus and the other is complementary to the positive (+) strand. Annealing the primers to denatured nucleic acid followed by extension with an enzyme, such as the large fragment of DNA Polymerase I and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers of the disclosure may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066.

Any nucleic acid specimen, in purified or non-purified form, can be utilized as the starting nucleic acid or acids, provided it contains, or is suspected of containing, the specific nucleic acid sequence containing the target locus (e.g., CpG). Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid that contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the target locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

The nucleic acid-containing specimen used for detection of methylated CpG may be from any source including brain, colon, urogenital, hematopoietic, thymus, testis, ovarian, uterine, prostate, breast, colon, lung and renal tissue and may be extracted by a variety of techniques such as that described by Maniatis, et al. (Molecular Cloning: A Laboratory Manual, Cold Spring Harbor, N.Y., pp 280, 281, 1982).

If the extracted sample is impure (such as plasma, serum, or blood or a sample embedded in paraffin), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80 to 100° C., for times ranging from about 15 seconds to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-'Quantitative Biology, 43:63 (1978)) and techniques for using RecA are reviewed in C. Radding (Ann. Rev. Genetics, 16:405-437 (1982)).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7-9, most preferably about 8. Preferably, a molar excess (for genomic nucleic acid, usually about $10^8$:1 primer: template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. Large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90-100° C. from about 15 seconds to 10 minutes, preferably from 1 to 4 minutes. After this heating period, the solution is allowed to cool to hybridization temperature primers specific Tm, which is preferable for the primer hybridization. To the mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at Tm temperature up to a temperature above which the agent for polymerization no longer functions.

The agent for polymerization may be any compound or system, which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products that are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

In some embodiments, the method of amplifying is by PCR, as described herein and as is commonly used by those of ordinary skill in the art. Alternative methods of amplification have been described and can also be employed as long as the methylated and non-methylated loci amplified by PCR using the primers of the invention is similarly amplified by the alternative.

The amplified products may be identified as methylated or non-methylated by sequencing. Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., *Rio/Technology,* 3:1008-1012 (1985)), allele-specific oligonucleotide (ASO) probe analysis (Conner, et al., *Proc. Natl. Acad. Sci. USA,* 80:278 (1983)), oligonucleotide ligation assays (OLAs) (Landegren, et al., *Science,* 241:1077 (1988)), and the like. Molecular techniques for DNA analysis have been reviewed (Landegren, et al., *Science,* 242:229-237 (1988)).

Optionally, the methylation pattern of the nucleic acid can be confirmed by restriction enzyme digestion and Southern blot analysis. Examples of methylation sensitive restriction endonucleases that can be used to detect 5' CpG methylation include SmaI, SacII, EagI, MspI, HpaII, BstUI and BssHII, for example.

The amplified products may be quantitatively assessed for methylation by sequencing, using for example, capillary sequencing, (briefly, the treated amplified DNA is amplified by either forward or reverse primers in the presence of dideoxyribonucleotides that stop the sequencing reaction and subjected to capillary electrophoresis to read the target sequence), high-throughput sequencing (sequencing by synthesis (Applied Biosystems), pyrosequencing (454 Roche Diagnostics) or by other technologies such as from Illumina, Pacific Bio and Helicos.

V. Exemplary Determinations of Methylation Values

In embodiments of the disclosure, identification of methylation parameters of any kind for one or more particular MRs allows screening, diagnosing, and/or prognosticating CRC in an individual. In some cases, quantification of methylation of one or more MRs allows screening, diagnosing, and/or prognosticating CRC in an individual.

In certain aspects of the disclosure, there is measuring of methylation in a relative or absolute manner for each individual, marker and sample type (e.g., serum, urine, and so forth). In exemplary embodiments, methylation is measured by any of the above-referenced exemplary methods. The results of such an exemplary measurement may be provided as a percent ranging from 0% (no methylation) to 100% (full methylation, in an absolute way). To compute the above-mentioned methylation score, the measurements provide the number of methylated nucleotides within individual MRs. In some cases, there is a specific value that can be compared to normal subjects (subjects that are cancer-free, for example in the same age range) values (in a relative way), for example.

In specific aspects of the disclosure, MRs that are methylated in cancer are utilized, for example, given that MRs in individuals without cancer are expected to be less methylated than in individuals with cancer.

A threshold for methylation score for a set of MRs may be determined, in some embodiments. One can observe the methylation scores in the population with CRC and one can take the maximum threshold against which non-cancer and cancer individuals can be distinguished.

In specific embodiments, for a given sample type the threshold for the methylation score may differ from sample type to sample type.

In certain embodiments of the disclosure, an individual is assayed for a certain number of MRs to obtain methylation level for each MR. Then, based on these figures, one can with a high accuracy distinguish between "cancer" or "non-cancer" case using methylation score for the set of MRs.

VI. Kits of the Disclosure

Any of the compositions described herein may be part of a kit. In a non-limiting example, one or more reagents to determine methylation level of one or more MRs may be in the kit in suitable container means. The reagents may include primers, buffers, dinucleotides, labels, dyes, sequencing reagents, and/or microchips comprising one or more nucleic acids associated with the invention, one or more PCR reagents, and so forth.

The kit may include primers that target one or more MRs described herein. This kit may be used in combination with any commercially available kit used for methylation quantification, such as QPCR SYBR® green Kit, QPCRTaqman KIT, QPCR HRM kit, QPCR FRET Kit, emulsion PCR KIT, high throughput library preparation kit, sequencing kit, hybridization kit for microarray or any software or script identifying the methylation of the MRs cited below, for example.

The kits can include a suitably aliquoted probes or primers disclosed herein, where appropriate. The components of the kits may be packaged either in aqueous media or in lyophilized form. However, the components of the kit may be provided as dried powder(s). When reagents and/or components are provided as a dry powder, the powder can be reconstituted by the addition of a suitable solvent. It is envisioned that the solvent may also be provided in another container means.

The container means of the kits will generally include at least one vial, test tube, flask, bottle, syringe or other container means, into which a component may be placed, and in some embodiments, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the targeting peptide and/or active agent and any other reagent containers in close confinement for commercial sale. Such containers may include injection or blow molded plastic containers into which the desired vials are retained. The container means may itself be a syringe, pipette, and/or other such like apparatus, from which the formulation may be applied to the sample collected from the body.

In some embodiments, there are devices suitable for extraction of a sample from an individual, including by non-invasive means, for example. Such devices include swab (including rectal swab), phlebotomy material(s), scalpel, syringe, rod, and so forth.

The sample from an individual can be assayed in tissue, blood, serum, plasma, spittle, stool, urine, or any other body fluid, for example. In some aspects, the disclosure uses any appropriate method to extract and concentrate nucleic acids from body fluids or any method to assess methylation directly from the body fluids. Methods to target the specific nucleic acids that correspond to one or more of the MRs are well known in the art. Furthermore, methods to quantify the level of methylation of the target sequences are also well known in the art.

The kit could also comprise any script or software using the analysis of the MRs described herein.

EXAMPLE

Description of Method and Results from the Clinical Study

The following example is included to demonstrate some embodiments of the invention. It should be appreciated by those of skill in the art that the techniques disclosed in the examples which follow represent techniques discovered by the inventor to function well in the practice of the invention, and thus can be considered to constitute some modes for its practice. However, those of skill in the art should, in light of the present disclosure, appreciate that many changes can be made in the specific embodiments which are disclosed and still obtain a like or similar result without departing from the spirit and scope of the invention.

In the present example, one or more biomarkers are identified for screening, diagnosis, and/or prognosis of CRC. The inventors designed a clinical study where 50 individuals with CRC provided both one cancerous and one non-cancerous (adjacent to the cancerous lesion) colon tissue samples. 25 patients had stage 1 CRC, while the other 25 patients had stage 2 CRC. Thus, both groups had an early stage CRC. These samples were assayed through bisulfite sequencing using Illumina TrueSelect DNA capturing protocol followed by Illumina sequencing. The inventors performed the analysis of the set of 176 MRs (defined in Table 1) as biomarkers whose methylation profiles enable accurate screening, diagnosis and/or prognosis of CRC. These are determined to capture cancer population diversity present in the 50 individuals that participated in the study. Table 2 below shows how the sensitivity changes with the methylation score threshold, while always ensuring 100% specificity for every threshold value. This means, Table 2 shows, as an illustration, the change of sensitivity with the methylation score keeping zero false positive predictions.

TABLE 2

Change of sensitivity when mSCORE threshold changes while keeping specificity at 100% (i.e., no false positives).

| mSCORE is greater than | Sensitivity |
|---|---|
| 577 | 100% |
| 783 | 98% |
| 1586 | 96% |
| 1709 | 94% |
| 2071 | 92% |
| 2449 | 90% |
| 2855 | 88% |
| 3015 | 86% |
| 3149 | 84% |
| 4982 | 82% |
| 6659 | 80% |
| 9449 | 78% |
| 9775 | 76% |
| 10049 | 74% |
| 10649 | 72% |
| 11947 | 70% |
| 14048 | 68% |
| 15737 | 66% |
| 16679 | 64% |
| 17687 | 62% |
| 19970 | 60% |
| 21167 | 58% |
| 24049 | 56% |
| 24600 | 54% |
| 26949 | 52% |
| 27116 | 50% |
| 29259 | 48% |
| 29839 | 46% |
| 38415 | 44% |
| 40742 | 42% |
| 44624 | 40% |
| 50665 | 38% |
| 51323 | 36% |
| 55544 | 34% |
| 58983 | 32% |
| 61109 | 30% |
| 61609 | 28% |
| 62467 | 26% |
| 66154 | 24% |
| 72929 | 22% |
| 75257 | 20% |
| 77102 | 18% |
| 77371 | 16% |
| 81362 | 14% |
| 84410 | 12% |
| 86272 | 10% |
| 91427 | 8% |
| 106623 | 6% |
| 109849 | 4% |
| 123025 | 2% |

The methylation pattern of the 176 MRs enables one to discriminate patients of the study from healthy controls with 100% of specificity and 100% of sensitivity if the methylation score calculated based on equation (1) is above the threshold of 577, as can be seen from the first data row of Table 2.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope embodiments under such processes, machines, manufacture, compositions of matter, means, methods, or steps.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

We claim:

1. A method of treating colorectal cancer (CRC) in a human subject, comprising:
   (a) assaying genomic nucleic acids from a sample comprising genomic DNA obtained from the human subject for the number of methylated nucleotides in the methylatable regions (MRs) of genomic DNA comprising SEQ ID NOs: 1-176,
   wherein the sample is selected from the group comprising tissue, blood, spittle, serum, plasma, urine, sputum, biopsy, and stool;
   (b) determining the methylation score (mSCORE) as defined by equation (1):

$$mSCORE = COV\ (coverage) \times mTOT\ (total\ methylation), \quad (1)$$

wherein the human subject is diagnosed as having colorectal cancer if the mSCORE within these 176 MRs as defined by equation (1) is greater than 577, and
   (c) treating the diagnosed human for CRC with an anticancer treatment.

2. A method of of treating colorectal cancer (CRC) in a human subject comprising,
   (a) assaying genomic nucleic acids from a colon biopsy sample obtained from the human subject for the number of methylated nucleotides in the methylatable regions (MRs) of genomic DNA comprising SEQ ID NOs: 1-176, wherein the human subject is diagnosed as having colorectal cancer if the methylation score within these 176 MRs as defined by equation (1) (mSCORE=COV (coverage)×mTOT (total methylation; is greater than 577, and
   (b) treating the human for CRC with an anticancer treatment.

3. The method of claim 1, wherein the human subject is 50 years or older in age.

4. The method of claim 1, wherein the human subject has one or more symptoms of colorectal cancer, is asymptomatic for colorectal cancer, has a prior history of colorectal cancer or, has not had a prior history of having colorectal cancer.

5. The method of claim 4, wherein the one or more symptoms is selected from the group consisting of a change in bowel habits, constipation that lasts more than about two weeks, diarrhea that lasts more than about two weeks, a feeling that the bowel does not empty completely, blood in the stool, narrow or thinner than normal stool, abdominal discomfort, gas pains, bloating, fullness, cramps, weight loss, fatigue, anemia, and a combination thereof.

6. The method of claim 1, wherein the human subject has a personal history of colorectal cancer, has a family history of colorectal cancer, has colon polyps, has had colon polyps, has inflammatory bowel disease, is positive for hemoccult test, was positive for hemoccult test, or a combination thereof.

7. The method of claim 1, wherein the human subject has a personal or family history of familial adenomatous polyposis, Lynch syndrome, Peutz-Jeghers syndrome or juvenile polyposis syndrome.

8. The method of claim 1, wherein the human subject is further subjected to stool testing, barium enema, virtual colonoscopy, sigmoidoscopy, and/or colonoscopy.

9. The method of claim 1, wherein the treatment for colorectal cancer comprises surgery, chemotherapy, radiation, immunotherapy, gene therapy, or a combination thereof and optionally, wherein the chemotherapy is selected from the group consisting of fluorouracil, bevacizumab, irinotecan, capecitabine, cetuximab, oxaliplatin, cetuximab leucovorin, panitumumab, and a combination thereof.

10. A method of treating-colorectal cancer (CRC) in a human subject, comprising administering to a therapeutic agent for treating CRC to the subject wherein the subject has been diagnosed has having colorectal cancer by a method comprising the steps of (a) assaying genomic nucleic acids from a sample comprising genomic DNA obtained from the human subject for the number of methylated nucleotides in the methylatable regions (MRs) of genomic DNA comprising SEQ ID NOs: 1-176; and (b) determining the methylation score (mSCORE) as defined by equation (1):

$$mSCORE = COV \text{ (coverage)} \times mTOT \text{ (total methylation)}, \quad (1)$$

wherein:
the human subject is diagnosed as having colorectal cancer if the mSCORE within these 176 MRs as defined by equation (1) is greater than 577, wherein the sample is selected from the group comprising tissue, blood, spittle, serum, plasma, urine, sputum, biopsy, and stool.

* * * * *

```
                        SEQUENCE LISTING

<160> NUMBER OF SEQ ID NOS: 176

<210> SEQ ID NO 1
<211> LENGTH: 50
<212> TYPE: DNA
<213> ORGANISM: Homo sapiens

<400> SEQUENCE: 1
cgggagcgcc ttcgtccccg cgcgcacctc cccgggtcgg gcgacttacg             50

<210> SEQ ID NO 2
<211> LENGTH: 50
<212> TYPE: DNA
<213> ORGANISM: Homo sapiens

<400> SEQUENCE: 2
acttgagatt taatcgactt caaaaccgta cacacagtcg cggcggtaat             50

<210> SEQ ID NO 3
<211> LENGTH: 50
<212> TYPE: DNA
<213> ORGANISM: Homo sapiens

<400> SEQUENCE: 3
ggaaagaatg cagatttgag gacccgcccg cgcgctcgga gcgccccact             50

<210> SEQ ID NO 4
<211> LENGTH: 50
<212> TYPE: DNA
<213> ORGANISM: Homo sapiens

<400> SEQUENCE: 4
ctgggctgcg gatccggcgc aggcggcccc ggacgctgct aggcgcgggc             50

<210> SEQ ID NO 5
<211> LENGTH: 50
<212> TYPE: DNA
<213> ORGANISM: Homo sapiens

<400> SEQUENCE: 5
ggcaccttcc ccgggggcct ggcgggcgac ttttctttcg ggaggcggcc             50

<210> SEQ ID NO 6
<211> LENGTH: 50
<212> TYPE: DNA
<213> ORGANISM: Homo sapiens

<400> SEQUENCE: 6
gcgggagccc cttccgggga acacgctctc cgggccgcgc agccgggcga             50

<210> SEQ ID NO 7
<211> LENGTH: 50
<212> TYPE: DNA
<213> ORGANISM: Homo sapiens

<400> SEQUENCE: 7
cccgtcttgc cgtagttgcg cagcgcgcgc gccatcttct ggtaggtcat             50
```

```
<210> SEQ ID NO 8
<211> LENGTH: 50
<212> TYPE: DNA
<213> ORGANISM: Homo sapiens

<400> SEQUENCE: 8
gggcccaccg gtcccacccc ggcgatcccc gcggcctcac cttggcacga      50

<210> SEQ ID NO 9
<211> LENGTH: 50
<212> TYPE: DNA
<213> ORGANISM: Homo sapiens

<400> SEQUENCE: 9
ccaccggtcc caccccggcg atccccgcgg cctcaccttg gcacgagcgc      50

<210> SEQ ID NO 10
<211> LENGTH: 50
<212> TYPE: DNA
<213> ORGANISM: Homo sapiens

<400> SEQUENCE: 10
tcccaccccg gcgatccccg cggcctcacc ttggcacgag cgcacgggta      50

<210> SEQ ID NO 11
<211> LENGTH: 50
<212> TYPE: DNA
<213> ORGANISM: Homo sapiens

<400> SEQUENCE: 11
tctacggcga ctccaggtta gtgcgggcag cgccggccgc gcggccgtga      50

<210> SEQ ID NO 12
<211> LENGTH: 50
<212> TYPE: DNA
<213> ORGANISM: Homo sapiens

<400> SEQUENCE: 12
tccaatgtga aattcccggg gaaggtcgcg agccgctagg ggccgttcgt      50

<210> SEQ ID NO 13
<211> LENGTH: 50
<212> TYPE: DNA
<213> ORGANISM: Homo sapiens

<400> SEQUENCE: 13
gaaatggacc gagcggaccc gccgccgcac gcaccctgct ccactccaag      50

<210> SEQ ID NO 14
<211> LENGTH: 50
<212> TYPE: DNA
<213> ORGANISM: Homo sapiens

<400> SEQUENCE: 14
ctcctaaggg ctcctggcgc gccgcgtagc cttggcgagg tccgcgctgg      50

<210> SEQ ID NO 15
<211> LENGTH: 50
<212> TYPE: DNA
<213> ORGANISM: Homo sapiens

<400> SEQUENCE: 15
ccgcccgcct ccttcgggat cgaatcaagg gctcccatag tgttaggagg      50
```

<210> SEQ ID NO 16
<211> LENGTH: 50
<212> TYPE: DNA
<213> ORGANISM: Homo sapiens

<400> SEQUENCE: 16
gggcgagagt gctgtttatc gtcatttgcc tcggagcttc gagagagggt          50

<210> SEQ ID NO 17
<211> LENGTH: 50
<212> TYPE: DNA
<213> ORGANISM: Homo sapiens

<400> SEQUENCE: 17
ggtattttgc ttttccgccc cgcatcctcc ggaactccct gcaccggaga          50

<210> SEQ ID NO 18
<211> LENGTH: 50
<212> TYPE: DNA
<213> ORGANISM: Homo sapiens

<400> SEQUENCE: 18
aggaacattt tcgccgtagc tgctccgtaa agcgattgtc caactgagag          50

<210> SEQ ID NO 19
<211> LENGTH: 50
<212> TYPE: DNA
<213> ORGANISM: Homo sapiens

<400> SEQUENCE: 19
gggcgtcgga cgagtggacc agggcggcga gtttgcccgg cgcgtctcgg          50

<210> SEQ ID NO 20
<211> LENGTH: 50
<212> TYPE: DNA
<213> ORGANISM: Homo sapiens

<400> SEQUENCE: 20
atgctgctgc ggcggccgcc gcggctcccg ccagggcact gcaaagacga          50

<210> SEQ ID NO 21
<211> LENGTH: 50
<212> TYPE: DNA
<213> ORGANISM: Homo sapiens

<400> SEQUENCE: 21
gggggttggg gggaccgggt gggggaggcc gggggtgcgg ggatgctgtc          50

<210> SEQ ID NO 22
<211> LENGTH: 50
<212> TYPE: DNA
<213> ORGANISM: Homo sapiens

<400> SEQUENCE: 22
cgggaccctg agcttccccc ggcgtctctc ggcgcttttc cgatctctag          50

<210> SEQ ID NO 23
<211> LENGTH: 50
<212> TYPE: DNA
<213> ORGANISM: Homo sapiens

<400> SEQUENCE: 23
ttctaccccc gtatcacttt ctatttctct gcagcgtgca tcgatcgccc        50

<210> SEQ ID NO 24
<211> LENGTH: 50
<212> TYPE: DNA
<213> ORGANISM: Homo sapiens

<400> SEQUENCE: 24
tgggcgtgag ggagacgcgc gctccggtgg gggggccgct tgggtccccc        50

<210> SEQ ID NO 25
<211> LENGTH: 50
<212> TYPE: DNA
<213> ORGANISM: Homo sapiens

<400> SEQUENCE: 25
tggagaacgg cggtgccatg accgtcagag gaggcgatga ggcccgggca        50

<210> SEQ ID NO 26
<211> LENGTH: 50
<212> TYPE: DNA
<213> ORGANISM: Homo sapiens

<400> SEQUENCE: 26
ttgcctttcc gaggggacaa cttccctcgg gctccagccc cagccccgac        50

<210> SEQ ID NO 27
<211> LENGTH: 50
<212> TYPE: DNA
<213> ORGANISM: Homo sapiens

<400> SEQUENCE: 27
gtcttttcgg gcagccaatt tcacacgcgc ctgtgtgcgg ttccgggcat        50

<210> SEQ ID NO 28
<211> LENGTH: 50
<212> TYPE: DNA
<213> ORGANISM: Homo sapiens

<400> SEQUENCE: 28
cccagtaagc tctagcaccc gggcgcgggt aacgggaagc gcagaaccaa        50

<210> SEQ ID NO 29
<211> LENGTH: 50
<212> TYPE: DNA
<213> ORGANISM: Homo sapiens

<400> SEQUENCE: 29
cacctccgag ggggcatgag atcggagaaa tcccttacgc tggcggcgcc        50

<210> SEQ ID NO 30
<211> LENGTH: 50
<212> TYPE: DNA
<213> ORGANISM: Homo sapiens

<400> SEQUENCE: 30
tgtcatcagt tgttcgagga agctcgcgca tgacgcgaca cttgccgtct        50

<210> SEQ ID NO 31
<211> LENGTH: 50
<212> TYPE: DNA
<213> ORGANISM: Homo sapiens

<400> SEQUENCE: 31
gtgaggtcgg cgccgcgctc cggagagtcg gttcctcccg attcagaccc    50

<210> SEQ ID NO 32
<211> LENGTH: 50
<212> TYPE: DNA
<213> ORGANISM: Homo sapiens

<400> SEQUENCE: 32
cggccagggg cgcggggcgc acggcgggcc cggggcaggt aagcgcaggt    50

<210> SEQ ID NO 33
<211> LENGTH: 50
<212> TYPE: DNA
<213> ORGANISM: Homo sapiens

<400> SEQUENCE: 33
gggcttctgc gccgcccgaa cgctaagttg cccctccgcg tggggggccg    50

<210> SEQ ID NO 34
<211> LENGTH: 50
<212> TYPE: DNA
<213> ORGANISM: Homo sapiens

<400> SEQUENCE: 34
ccggcgcccc agagaagttc ggggagcggt gagcctagcc gccgcgcgct    50

<210> SEQ ID NO 35
<211> LENGTH: 50
<212> TYPE: DNA
<213> ORGANISM: Homo sapiens

<400> SEQUENCE: 35
ggccgcttct ccgactctgt gagcagtttc cactcggcgc ccaagcgctt    50

<210> SEQ ID NO 36
<211> LENGTH: 50
<212> TYPE: DNA
<213> ORGANISM: Homo sapiens

<400> SEQUENCE: 36
caccgcgctg tccccgcgtc tcgcggaccg agaccggcgg tgaggatggg    50

<210> SEQ ID NO 37
<211> LENGTH: 50
<212> TYPE: DNA
<213> ORGANISM: Homo sapiens

<400> SEQUENCE: 37
gaccagcgcg cggtggccgg ccctgcccta cggcggtaag cgactttctg    50

<210> SEQ ID NO 38
<211> LENGTH: 50
<212> TYPE: DNA
<213> ORGANISM: Homo sapiens

<400> SEQUENCE: 38
gcgtcttggc ggtaagtcct ggctcccgcg cttggacttg cgcgcccgag    50

<210> SEQ ID NO 39
<211> LENGTH: 50
<212> TYPE: DNA
<213> ORGANISM: Homo sapiens

<400> SEQUENCE: 39
cgctgggggg cgcacaggcc atggaggccg cacccgcggc ggcggcggcc    50

<210> SEQ ID NO 40
<211> LENGTH: 50
<212> TYPE: DNA
<213> ORGANISM: Homo sapiens

<400> SEQUENCE: 40
cagcgcgccc aggagtgcgc cggagattcg gaaacccgca gagacttctc    50

<210> SEQ ID NO 41
<211> LENGTH: 50
<212> TYPE: DNA
<213> ORGANISM: Homo sapiens

<400> SEQUENCE: 41
cggagccgga ggagaacaag cggacgcgca cggcctacac gcgcgcacag    50

<210> SEQ ID NO 42
<211> LENGTH: 50
<212> TYPE: DNA
<213> ORGANISM: Homo sapiens

<400> SEQUENCE: 42
acggcggctc ggcggccggc gtttcggcgg cacagtcaca atgcaagtcc    50

<210> SEQ ID NO 43
<211> LENGTH: 50
<212> TYPE: DNA
<213> ORGANISM: Homo sapiens

<400> SEQUENCE: 43
gcagaccccc acggacgcgc cagctccgcc gcgctcgctg acagcccgc    50

<210> SEQ ID NO 44
<211> LENGTH: 50
<212> TYPE: DNA
<213> ORGANISM: Homo sapiens

<400> SEQUENCE: 44
cgccgccgcg gctccggctc gtctccatgg aaaccgcgcg ggataagccg    50

<210> SEQ ID NO 45
<211> LENGTH: 50
<212> TYPE: DNA
<213> ORGANISM: Homo sapiens

<400> SEQUENCE: 45
gctcactttc ctccgcgttg cttccggacg gcgccgaccg ccggagccca    50

<210> SEQ ID NO 46
<211> LENGTH: 50
<212> TYPE: DNA
<213> ORGANISM: Homo sapiens

<400> SEQUENCE: 46
cggcgcgcgc tcccaccttt gccgcacact ccggcgagcc gagcccgcag    50

<210> SEQ ID NO 47
<211> LENGTH: 50
<212> TYPE: DNA
<213> ORGANISM: Homo sapiens

<400> SEQUENCE: 47
ccctgcatgc gggccgcgca ccgcgctgtc cccgcgtctc gcggaccgag         50

<210> SEQ ID NO 48
<211> LENGTH: 50
<212> TYPE: DNA
<213> ORGANISM: Homo sapiens

<400> SEQUENCE: 48
gcggtaagcg actttctgcc tggtccccgt gggtcacgcg cgcatggacc         50

<210> SEQ ID NO 49
<211> LENGTH: 50
<212> TYPE: DNA
<213> ORGANISM: Homo sapiens

<400> SEQUENCE: 49
ccccgccctc actgtctcgc ctgttgcgcc cggagtgagg gcgacccggg         50

<210> SEQ ID NO 50
<211> LENGTH: 50
<212> TYPE: DNA
<213> ORGANISM: Homo sapiens

<400> SEQUENCE: 50
cagttctagc gtcaacccgg tgctctacgt cttcaccgct ggagatctgc         50

<210> SEQ ID NO 51
<211> LENGTH: 50
<212> TYPE: DNA
<213> ORGANISM: Homo sapiens

<400> SEQUENCE: 51
acctggccct gcagcgccgc ggggctggcg gcgtggtgcg ccaggtccgg         50

<210> SEQ ID NO 52
<211> LENGTH: 50
<212> TYPE: DNA
<213> ORGANISM: Homo sapiens

<400> SEQUENCE: 52
caatccccgc cctcactgtc tcgcctgttg cgcccggagt gagggcgacc         50

<210> SEQ ID NO 53
<211> LENGTH: 50
<212> TYPE: DNA
<213> ORGANISM: Homo sapiens

<400> SEQUENCE: 53
tgcggggcag cccgcgcctg tcacctggct ggcccaaccc agctggccct         50

<210> SEQ ID NO 54
<211> LENGTH: 50
<212> TYPE: DNA
<213> ORGANISM: Homo sapiens

<400> SEQUENCE: 54
gacgccttcc gcgcgcactg cccgcgcctg cgcacctata ccctcaagct         50

<210> SEQ ID NO 55
<211> LENGTH: 50
<212> TYPE: DNA

<213> ORGANISM: Homo sapiens

<400> SEQUENCE: 55
actgtggtcg ctccaggcta ggcctcggag cccgttctgg cctggcctcg    50

<210> SEQ ID NO 56
<211> LENGTH: 50
<212> TYPE: DNA
<213> ORGANISM: Homo sapiens

<400> SEQUENCE: 56
ccgcgcgcac tgcccgcgcc tgcgcaccta taccctcaag ctcacgcgcg    50

<210> SEQ ID NO 57
<211> LENGTH: 50
<212> TYPE: DNA
<213> ORGANISM: Homo sapiens

<400> SEQUENCE: 57
cgctccaggc taggcctcgg agcccgttct ggcctggcct cgacccatat    50

<210> SEQ ID NO 58
<211> LENGTH: 50
<212> TYPE: DNA
<213> ORGANISM: Homo sapiens

<400> SEQUENCE: 58
ccttccgcgc gcactgcccg cgcctgcgca cctataccct caagctcacg    50

<210> SEQ ID NO 59
<211> LENGTH: 50
<212> TYPE: DNA
<213> ORGANISM: Homo sapiens

<400> SEQUENCE: 59
cgcgagccgc atccctggag gcctacgctc gtggcgtgat tgggcgactt    50

<210> SEQ ID NO 60
<211> LENGTH: 50
<212> TYPE: DNA
<213> ORGANISM: Homo sapiens

<400> SEQUENCE: 60
tggtcgctcc aggctaggcc tcggagcccg ttctggcctg gcctcgaccc    50

<210> SEQ ID NO 61
<211> LENGTH: 50
<212> TYPE: DNA
<213> ORGANISM: Homo sapiens

<400> SEQUENCE: 61
gcgtggtgag ccactcggtg ctggacgcct ccgcgcgca ctgcccgcgc    50

<210> SEQ ID NO 62
<211> LENGTH: 50
<212> TYPE: DNA
<213> ORGANISM: Homo sapiens

<400> SEQUENCE: 62
gagcccgttc tggcctggcc tcgacccata tccccgtaag cggcaggcct    50

<210> SEQ ID NO 63
<211> LENGTH: 50

<212> TYPE: DNA
<213> ORGANISM: Homo sapiens

<400> SEQUENCE: 63
gaggggcttt ctgttcgcag cggagggtct cagcggctac gcggtgcggt         50

<210> SEQ ID NO 64
<211> LENGTH: 50
<212> TYPE: DNA
<213> ORGANISM: Homo sapiens

<400> SEQUENCE: 64
gccggccccg gaggcctcgg agcgccgggc ctaccggacg tttgcggcga         50

<210> SEQ ID NO 65
<211> LENGTH: 50
<212> TYPE: DNA
<213> ORGANISM: Homo sapiens

<400> SEQUENCE: 65
acgcggcgcc gcatcaagcc gtggcggaga tcgacgcgct ctacgacgtg         50

<210> SEQ ID NO 66
<211> LENGTH: 50
<212> TYPE: DNA
<213> ORGANISM: Homo sapiens

<400> SEQUENCE: 66
gcctgtgggt tcagggaagt gttaccaacc attgcgcgca ggtgggcgcg         50

<210> SEQ ID NO 67
<211> LENGTH: 50
<212> TYPE: DNA
<213> ORGANISM: Homo sapiens

<400> SEQUENCE: 67
gcactgcccg cgcctgcgca cctataccct caagctcacg cgcgagccgc         50

<210> SEQ ID NO 68
<211> LENGTH: 50
<212> TYPE: DNA
<213> ORGANISM: Homo sapiens

<400> SEQUENCE: 68
cgcgtgtgtg agggcgtgtg tccccacagg aggaatatg tgtgcgcagg          50

<210> SEQ ID NO 69
<211> LENGTH: 50
<212> TYPE: DNA
<213> ORGANISM: Homo sapiens

<400> SEQUENCE: 69
gcgtcggtgc tgcgtgcccc gccgcccgcc tgcaggtcga tgtaagagtg         50

<210> SEQ ID NO 70
<211> LENGTH: 50
<212> TYPE: DNA
<213> ORGANISM: Homo sapiens

<400> SEQUENCE: 70
gggctccagc ccgccggccc cgcgcagcgc gcagccggga ctcgacgcgc         50

<210> SEQ ID NO 71

```
<211> LENGTH: 50
<212> TYPE: DNA
<213> ORGANISM: Homo sapiens

<400> SEQUENCE: 71
cccgagtcca ggctggcgtc ggtgctgcgt gccccgccgc ccgcctgcag          50

<210> SEQ ID NO 72
<211> LENGTH: 50
<212> TYPE: DNA
<213> ORGANISM: Homo sapiens

<400> SEQUENCE: 72
tggcccgggc tccagcccgc cggccccgcg cagcgcgcag ccgggactcg          50

<210> SEQ ID NO 73
<211> LENGTH: 50
<212> TYPE: DNA
<213> ORGANISM: Homo sapiens

<400> SEQUENCE: 73
atttctagtc catcgcctta accactcggc cacgactacg aggcttaggg          50

<210> SEQ ID NO 74
<211> LENGTH: 50
<212> TYPE: DNA
<213> ORGANISM: Homo sapiens

<400> SEQUENCE: 74
ggcttggggg cgggtagcgg ggcaaagcgt cttcgggggc ggagatcagt          50

<210> SEQ ID NO 75
<211> LENGTH: 50
<212> TYPE: DNA
<213> ORGANISM: Homo sapiens

<400> SEQUENCE: 75
acctacgcgc gcaccttgcg ctacctctgg cgcgccgtcg accggtggc           50

<210> SEQ ID NO 76
<211> LENGTH: 50
<212> TYPE: DNA
<213> ORGANISM: Homo sapiens

<400> SEQUENCE: 76
tcgtcggcct ccgcccaggc ccctgtaatc cgcgcgccct ctccccgcag          50

<210> SEQ ID NO 77
<211> LENGTH: 50
<212> TYPE: DNA
<213> ORGANISM: Homo sapiens

<400> SEQUENCE: 77
gccggggtgg tgcagccgga aatccaggcg gctcaggatg cgacgctcgg          50

<210> SEQ ID NO 78
<211> LENGTH: 50
<212> TYPE: DNA
<213> ORGANISM: Homo sapiens

<400> SEQUENCE: 78
ccgccgaccg gcctgaccgc gcccgggctg ccctcgctca ggaccgtgga          50
```

<210> SEQ ID NO 79
<211> LENGTH: 50
<212> TYPE: DNA
<213> ORGANISM: Homo sapiens

<400> SEQUENCE: 79
cgcggggatg cgcgcgtcta cacccgcgat gtcccgggcc cataatttca            50

<210> SEQ ID NO 80
<211> LENGTH: 50
<212> TYPE: DNA
<213> ORGANISM: Homo sapiens

<400> SEQUENCE: 80
gcttccacgc ggggatgcgc gcgtctacac ccgcgatgtc ccgggcccat            50

<210> SEQ ID NO 81
<211> LENGTH: 50
<212> TYPE: DNA
<213> ORGANISM: Homo sapiens

<400> SEQUENCE: 81
agtaccttga gacagtactc gcgcacgcgc tcgtagttta ccagctccga            50

<210> SEQ ID NO 82
<211> LENGTH: 50
<212> TYPE: DNA
<213> ORGANISM: Homo sapiens

<400> SEQUENCE: 82
acacgaaagc ccgtgtggtc gcgccgggag ctcacggcgt tccaagcggc            50

<210> SEQ ID NO 83
<211> LENGTH: 50
<212> TYPE: DNA
<213> ORGANISM: Homo sapiens

<400> SEQUENCE: 83
gcgcccctgc gcgcgtgcca ctgggtcgca gcgcgatgcg gctgcgccgg            50

<210> SEQ ID NO 84
<211> LENGTH: 50
<212> TYPE: DNA
<213> ORGANISM: Homo sapiens

<400> SEQUENCE: 84
ggaaaacgtc ccagaggcgc gcgcggccct cgggcgcgcc cccggtctgc            50

<210> SEQ ID NO 85
<211> LENGTH: 50
<212> TYPE: DNA
<213> ORGANISM: Homo sapiens

<400> SEQUENCE: 85
cgccgggctc cacgtgcgcg atggcgttct cgctcaggtc cagctcctcc            50

<210> SEQ ID NO 86
<211> LENGTH: 50
<212> TYPE: DNA
<213> ORGANISM: Homo sapiens

<400> SEQUENCE: 86
agcgcgggca gcgcggccag gtcgcccggg ttcaggcagc ggatgcggtt            50

<210> SEQ ID NO 87
<211> LENGTH: 50
<212> TYPE: DNA
<213> ORGANISM: Homo sapiens

<400> SEQUENCE: 87
gcgcgtgcca ctgggtcgca gcgcgatgcg gctgcgccgg ctgcgggggt        50

<210> SEQ ID NO 88
<211> LENGTH: 50
<212> TYPE: DNA
<213> ORGANISM: Homo sapiens

<400> SEQUENCE: 88
aggcgccggg ctccacgtgc gcgatggcgt tctcgctcag gtccagctcc        50

<210> SEQ ID NO 89
<211> LENGTH: 50
<212> TYPE: DNA
<213> ORGANISM: Homo sapiens

<400> SEQUENCE: 89
tccagcgcgg gcagcgcggc caggtcgccc gggttcaggc agcggatgcg        50

<210> SEQ ID NO 90
<211> LENGTH: 50
<212> TYPE: DNA
<213> ORGANISM: Homo sapiens

<400> SEQUENCE: 90
ggtggctcat cgcggtcacg gacttccaga cgcgctcgcg cttgctgcgc        50

<210> SEQ ID NO 91
<211> LENGTH: 50
<212> TYPE: DNA
<213> ORGANISM: Homo sapiens

<400> SEQUENCE: 91 gaccccctccg cttccacgcg gggatgcgcg cgtctacacc cgcgatgtcc       50

<210> SEQ ID NO 92
<211> LENGTH: 50
<212> TYPE: DNA
<213> ORGANISM: Homo sapiens

<400> SEQUENCE: 92
tcgcagacac cggggctggg tttctctttc ctcttttggg agaaaaggaa        50

<210> SEQ ID NO 93
<211> LENGTH: 50
<212> TYPE: DNA
<213> ORGANISM: Homo sapiens

<400> SEQUENCE: 93
gtgggagtcc tgggccgctc acgccgcacc cctgcaacga gctggggccc        50

<210> SEQ ID NO 94
<211> LENGTH: 50
<212> TYPE: DNA
<213> ORGANISM: Homo sapiens

<400> SEQUENCE: 94
cgccggctcc gagggtgagt gacagccgga gaggccaagc tggacacgcc        50

<210> SEQ ID NO 95
<211> LENGTH: 50
<212> TYPE: DNA
<213> ORGANISM: Homo sapiens

<400> SEQUENCE: 95
ggtacgcgcc gagcaagaac ccgcacggag ccggcgcgcc gcggctgggc            50

<210> SEQ ID NO 96
<211> LENGTH: 50
<212> TYPE: DNA
<213> ORGANISM: Homo sapiens

<400> SEQUENCE: 96
ccctggggcc cccttctgca gagcggggct ccggatctaa tctgatctaa            50

<210> SEQ ID NO 97
<211> LENGTH: 50
<212> TYPE: DNA
<213> ORGANISM: Homo sapiens

<400> SEQUENCE: 97
aacgcctttg tggtgtggct gctggccggg cggcggggcc cgcggcggct            50

<210> SEQ ID NO 98
<211> LENGTH: 50
<212> TYPE: DNA
<213> ORGANISM: Homo sapiens

<400> SEQUENCE: 98
catcttggtc tcggcggcgg cgacggcggc gaggacgcgg agcactctgg            50

<210> SEQ ID NO 99
<211> LENGTH: 50
<212> TYPE: DNA
<213> ORGANISM: Homo sapiens

<400> SEQUENCE: 99
tggcgctgtt ttcggtctct cctgaggtcg caaccctctt cccacgaaca            50

<210> SEQ ID NO 100
<211> LENGTH: 50
<212> TYPE: DNA
<213> ORGANISM: Homo sapiens

<400> SEQUENCE: 100
gtctccagac cttgggccgg cacgcgtgac acggcacttc aggctccacg            50

<210> SEQ ID NO 101
<211> LENGTH: 50
<212> TYPE: DNA
<213> ORGANISM: Homo sapiens

<400> SEQUENCE: 101
accggcgccg cgggacggaa gcgagcgggc gcgggcgccg cgcagatggc            50

<210> SEQ ID NO 102
<211> LENGTH: 50
<212> TYPE: DNA
<213> ORGANISM: Homo sapiens

<400> SEQUENCE: 102
cgtgggagtc ctgggccgct cacgccgcac ccctgcaacg agctggggcc    50

<210> SEQ ID NO 103
<211> LENGTH: 50
<212> TYPE: DNA
<213> ORGANISM: Homo sapiens

<400> SEQUENCE: 103
gattgatgaa attcgcatcc cgacccacg ggtgtcgaag tcatcacttc    50

<210> SEQ ID NO 104
<211> LENGTH: 50
<212> TYPE: DNA
<213> ORGANISM: Homo sapiens

<400> SEQUENCE: 104
cggcgtccct ggagcgcact atcactgggg ccacggaagg caggttttct    50

<210> SEQ ID NO 105
<211> LENGTH: 50
<212> TYPE: DNA
<213> ORGANISM: Homo sapiens

<400> SEQUENCE: 105
cacacacgtg tgtaaagttt gttccacgca gaaacaaagg acgcgtgggg    50

<210> SEQ ID NO 106
<211> LENGTH: 50
<212> TYPE: DNA
<213> ORGANISM: Homo sapiens

<400> SEQUENCE: 106
ggcgcagagt ccagcgtccg gctctcgagc tcaatcccgc gccccgacgg    50

<210> SEQ ID NO 107
<211> LENGTH: 50
<212> TYPE: DNA
<213> ORGANISM: Homo sapiens

<400> SEQUENCE: 107
gggccggggg cccgcgcggt cacggcttct cgtgacagtg tttgcaaagc    50

<210> SEQ ID NO 108
<211> LENGTH: 50
<212> TYPE: DNA
<213> ORGANISM: Homo sapiens

<400> SEQUENCE: 108
gcggagggcg tcccggagaa ggcggcgcac ttgtcagggc agggccccag    50

<210> SEQ ID NO 109
<211> LENGTH: 50
<212> TYPE: DNA
<213> ORGANISM: Homo sapiens

<400> SEQUENCE: 109
gcttgcgcat tgtggagctg gcgcagctgg gcatccgacc ctgtgacatc    50

<210> SEQ ID NO 110
<211> LENGTH: 50
<212> TYPE: DNA
<213> ORGANISM: Homo sapiens

<400> SEQUENCE: 110
catcgccacc gccgggctcc gctgcggctc ccgggctccg ccgggtgccc        50

<210> SEQ ID NO 111
<211> LENGTH: 50
<212> TYPE: DNA
<213> ORGANISM: Homo sapiens

<400> SEQUENCE: 111
gacaaggagc tggaggcgca gtgccggcgg cacggctacg cggccctgcg        50

<210> SEQ ID NO 112
<211> LENGTH: 50
<212> TYPE: DNA
<213> ORGANISM: Homo sapiens

<400> SEQUENCE: 112
ggcgcagtgc cggcggcacg gctacgcggc cctgcggccc cacctggtgg        50

<210> SEQ ID NO 113
<211> LENGTH: 50
<212> TYPE: DNA
<213> ORGANISM: Homo sapiens

<400> SEQUENCE: 113
ggcggcctag ccggagatgc acgcgctgta atagaccgcg ctgctggcgt        50

<210> SEQ ID NO 114
<211> LENGTH: 50
<212> TYPE: DNA
<213> ORGANISM: Homo sapiens

<400> SEQUENCE: 114
gctccgccgc gccccgtcc ccggacacct gcgccttcgc ctgttcttgg         50

<210> SEQ ID NO 115
<211> LENGTH: 50
<212> TYPE: DNA
<213> ORGANISM: Homo sapiens

<400> SEQUENCE: 115
ctcggagcgg cagccgtgca gccggctcac gcggcgcagc gggaagtcct        50

<210> SEQ ID NO 116
<211> LENGTH: 50
<212> TYPE: DNA
<213> ORGANISM: Homo sapiens

<400> SEQUENCE: 116
gcgccgggct atggacgcgg acgccggcga agcgcacccc gggacgtccg        50

<210> SEQ ID NO 117
<211> LENGTH: 50
<212> TYPE: DNA
<213> ORGANISM: Homo sapiens

<400> SEQUENCE: 117
tttaagaacc ggcggcagcg cgaccgcgcc gcggcggcca agaacaggtt        50

<210> SEQ ID NO 118
<211> LENGTH: 50
<212> TYPE: DNA
<213> ORGANISM: Homo sapiens

<400> SEQUENCE: 118
gctgtccacg tgcccgggcg ccgcccgagc gccacgcctg ctgtactcgc            50

<210> SEQ ID NO 119
<211> LENGTH: 50
<212> TYPE: DNA
<213> ORGANISM: Homo sapiens

<400> SEQUENCE: 119
ttcagacgct gctcaactcc atggcaccag acgcggcgcc ggcctcctgc            50

<210> SEQ ID NO 120
<211> LENGTH: 50
<212> TYPE: DNA
<213> ORGANISM: Homo sapiens

<400> SEQUENCE: 120
gcgccgcggc gcagcagcac gcgggttctg agaagcgcgt ggctccggcg            50

<210> SEQ ID NO 121
<211> LENGTH: 50
<212> TYPE: DNA
<213> ORGANISM: Homo sapiens

<400> SEQUENCE: 121
aaatttcgac ccggggcgcc ggcatcgcga cgctcagcca gtgcccgcga            50

<210> SEQ ID NO 122
<211> LENGTH: 50
<212> TYPE: DNA
<213> ORGANISM: Homo sapiens

<400> SEQUENCE: 122
gctggggcgt ctgccttccc tgctgctccg cgccgcagct gggcgccccg            50

<210> SEQ ID NO 123
<211> LENGTH: 50
<212> TYPE: DNA
<213> ORGANISM: Homo sapiens

<400> SEQUENCE: 123
tcgtagtcgt cgcacacctc gagcacgtcg cgctcggagc ggcagccgtg            50

<210> SEQ ID NO 124
<211> LENGTH: 50
<212> TYPE: DNA
<213> ORGANISM: Homo sapiens

<400> SEQUENCE: 124
cagccggctc acgcggcgca gcgggaagtc cttcagcagc tcccgggaca            50

<210> SEQ ID NO 125
<211> LENGTH: 50
<212> TYPE: DNA
<213> ORGANISM: Homo sapiens

<400> SEQUENCE: 125
tgaggtccca tcgcgccgcg acccccggac gctcctccgc gccgcccagg            50

<210> SEQ ID NO 126
<211> LENGTH: 50
<212> TYPE: DNA
<213> ORGANISM: Homo sapiens

```
<400> SEQUENCE: 126
ggggctccgg cggcggcgcg ggcgcgaccc atcccgctgg cgctccccgc        50

<210> SEQ ID NO 127
<211> LENGTH: 50
<212> TYPE: DNA
<213> ORGANISM: Homo sapiens

<400> SEQUENCE: 127
agtgtcgcgt ggctggcaat ccgcggcggc ctccggcgca tgcgcagttc        50

<210> SEQ ID NO 128
<211> LENGTH: 50
<212> TYPE: DNA
<213> ORGANISM: Homo sapiens

<400> SEQUENCE: 128
ccgagcgcgc cgcgcaggcg cacggcccgg ccgccgccgc cgtcgccgcc        50

<210> SEQ ID NO 129
<211> LENGTH: 50
<212> TYPE: DNA
<213> ORGANISM: Homo sapiens

<400> SEQUENCE: 129
cgtcgtgcga cccggagcag ggcgcgcggg agccctcgtc gcccttgggg        50

<210> SEQ ID NO 130
<211> LENGTH: 50
<212> TYPE: DNA
<213> ORGANISM: Homo sapiens

<400> SEQUENCE: 130
acacctgcgc gtctctcgcg cgccgggatc ctttctccca acgttttacc        50

<210> SEQ ID NO 131
<211> LENGTH: 50
<212> TYPE: DNA
<213> ORGANISM: Homo sapiens

<400> SEQUENCE: 131
aagctgacca cccgcggccc cgcgtacctt gcccttgtag gtgcggtcgg        50

<210> SEQ ID NO 132
<211> LENGTH: 50
<212> TYPE: DNA
<213> ORGANISM: Homo sapiens

<400> SEQUENCE: 132
cgtcgctgga gccgggaggc gccgggttcg gcggagcgcg gagcggggct        50

<210> SEQ ID NO 133
<211> LENGTH: 50
<212> TYPE: DNA
<213> ORGANISM: Homo sapiens

<400> SEQUENCE: 133
ctctcggccc cgctcccagc gggcgcgctg acaaaggccc gggagggata        50

<210> SEQ ID NO 134
<211> LENGTH: 50
<212> TYPE: DNA
```

<213> ORGANISM: Homo sapiens

<400> SEQUENCE: 134
tgagacgctg gcggacatct cgctgtcgct ccggcccgcg gcttcctcct        50

<210> SEQ ID NO 135
<211> LENGTH: 50
<212> TYPE: DNA
<213> ORGANISM: Homo sapiens

<400> SEQUENCE: 135
atttcttcgc gtgtggacat gtccgggtag cggttcctct ggaaagtggc        50

<210> SEQ ID NO 136
<211> LENGTH: 50
<212> TYPE: DNA
<213> ORGANISM: Homo sapiens

<400> SEQUENCE: 136
ctgctaaagc gtcctatgct tgcagcgcgg gccacggcgc tgacggtatc        50

<210> SEQ ID NO 137
<211> LENGTH: 50
<212> TYPE: DNA
<213> ORGANISM: Homo sapiens

<400> SEQUENCE: 137
ctccccgcgt cgccagagga ggctcccggc tgcggttccc gccctcggcc        50

<210> SEQ ID NO 138
<211> LENGTH: 50
<212> TYPE: DNA
<213> ORGANISM: Homo sapiens

<400> SEQUENCE: 138
gcggctccgt cccgggcgca ggcttgtcgc gccgaatcgc gcgctcgcgg        50

<210> SEQ ID NO 139
<211> LENGTH: 50
<212> TYPE: DNA
<213> ORGANISM: Homo sapiens

<400> SEQUENCE: 139
ggctccgtcc cgggcgcagg cttgtcgcgc cgaatcgcgc gctcgcggag        50

<210> SEQ ID NO 140
<211> LENGTH: 50
<212> TYPE: DNA
<213> ORGANISM: Homo sapiens

<400> SEQUENCE: 140
agacacgcgc gcgctcgcgc ttcccggaga ggtcggcgcg tctcgctgaa        50

<210> SEQ ID NO 141
<211> LENGTH: 50
<212> TYPE: DNA
<213> ORGANISM: Homo sapiens

<400> SEQUENCE: 141
atccccgagt agccacgcgg gcgccacttc agggacgcgg ggcggcggct        50

<210> SEQ ID NO 142
<211> LENGTH: 50

<212> TYPE: DNA
<213> ORGANISM: Homo sapiens

<400> SEQUENCE: 142
cgcgcacggc aggcccagat ccgcacagag acgcagacac gcgcgcgctc          50

<210> SEQ ID NO 143
<211> LENGTH: 50
<212> TYPE: DNA
<213> ORGANISM: Homo sapiens

<400> SEQUENCE: 143
caggcttgtc gcgccgaatc gcgcgctcgc ggaggctggg ccacggcctc          50

<210> SEQ ID NO 144
<211> LENGTH: 50
<212> TYPE: DNA
<213> ORGANISM: Homo sapiens

<400> SEQUENCE: 144
caccagcaaa aacggcgcgt aacccttgcg gcgccggccg aaccgcgcca          50

<210> SEQ ID NO 145
<211> LENGTH: 50
<212> TYPE: DNA
<213> ORGANISM: Homo sapiens

<400> SEQUENCE: 145
acggcgcgta acccttgcgg cgccggccga accgcgccag agctggcgcg          50

<210> SEQ ID NO 146
<211> LENGTH: 50
<212> TYPE: DNA
<213> ORGANISM: Homo sapiens

<400> SEQUENCE: 146
acccaccccg ggctggcagc aggacccgcc gggcctcctg cgcagcgcga          50

<210> SEQ ID NO 147
<211> LENGTH: 50
<212> TYPE: DNA
<213> ORGANISM: Homo sapiens

<400> SEQUENCE: 147
cgtgacctac acggagcacg ccaagcgcaa gacggtcacc gccatggacg          50

<210> SEQ ID NO 148
<211> LENGTH: 50
<212> TYPE: DNA
<213> ORGANISM: Homo sapiens

<400> SEQUENCE: 148
accgcgagga ggacgccgcg ctcttcaagg tctccggcct cgggagccgg          50

<210> SEQ ID NO 149
<211> LENGTH: 50
<212> TYPE: DNA
<213> ORGANISM: Homo sapiens

<400> SEQUENCE: 149
cccaggcgct ggagagcgcg gcgcgcgcgg gctccggacg cgcacccacc          50

<210> SEQ ID NO 150

```
<211> LENGTH: 50
<212> TYPE: DNA
<213> ORGANISM: Homo sapiens

<400> SEQUENCE: 150
gccgcggcgg cagcgctggg gtgctcggcg gattgggccg cgcacgcttt         50

<210> SEQ ID NO 151
<211> LENGTH: 50
<212> TYPE: DNA
<213> ORGANISM: Homo sapiens

<400> SEQUENCE: 151
gcacgccaag cgcaagacgg tcaccgccat ggacgtggtc tacgcgctca         50

<210> SEQ ID NO 152
<211> LENGTH: 50
<212> TYPE: DNA
<213> ORGANISM: Homo sapiens

<400> SEQUENCE: 152
gtgatccggg acgccgtgac ctacacggag cacgccaagc gcaagacggt         50

<210> SEQ ID NO 153
<211> LENGTH: 50
<212> TYPE: DNA
<213> ORGANISM: Homo sapiens

<400> SEQUENCE: 153
caccgccatg gacgtggtct acgcgctcaa gcgccagggc cgcaccctct         50

<210> SEQ ID NO 154
<211> LENGTH: 50
<212> TYPE: DNA
<213> ORGANISM: Homo sapiens

<400> SEQUENCE: 154
cgggacgccg tgacctacac ggagcacgcc aagcgcaaga cggtcaccgc         50

<210> SEQ ID NO 155
<211> LENGTH: 50
<212> TYPE: DNA
<213> ORGANISM: Homo sapiens

<400> SEQUENCE: 155
gacggtcacc gccatggacg tggtctacgc gctcaagcgc cagggccgca         50

<210> SEQ ID NO 156
<211> LENGTH: 50
<212> TYPE: DNA
<213> ORGANISM: Homo sapiens

<400> SEQUENCE: 156
tggcccctca acctgctgcg gccccggggt gggcccggct atgtggatgt         50

<210> SEQ ID NO 157
<211> LENGTH: 50
<212> TYPE: DNA
<213> ORGANISM: Homo sapiens

<400> SEQUENCE: 157
ggcaagattt atgactcggc gccccaaagc tgtaaacaga gcacaaaaca         50
```

<210> SEQ ID NO 158
<211> LENGTH: 50
<212> TYPE: DNA
<213> ORGANISM: Homo sapiens

<400> SEQUENCE: 158
gccgcggctg caggcggctc gcccaggcgc gcagccctcg gtcccacctc            50

<210> SEQ ID NO 159
<211> LENGTH: 50
<212> TYPE: DNA
<213> ORGANISM: Homo sapiens

<400> SEQUENCE: 159
tcttccgcag cgcggcgaac gcctcgttca gcgactgggt gcgctggcgc            50

<210> SEQ ID NO 160
<211> LENGTH: 50
<212> TYPE: DNA
<213> ORGANISM: Homo sapiens

<400> SEQUENCE: 160
gctgcgcctc cacgctcttc acggtgctta cgtacctggt ggacatgcgg            50

<210> SEQ ID NO 161
<211> LENGTH: 50
<212> TYPE: DNA
<213> ORGANISM: Homo sapiens

<400> SEQUENCE: 161
gagtcgtcga gtcgcacggc ccggcttgac acgctgcgcc ccgcgccccc            50

<210> SEQ ID NO 162
<211> LENGTH: 50
<212> TYPE: DNA
<213> ORGANISM: Homo sapiens

<400> SEQUENCE: 162
ctgttcccgg ccgggaaact gggtcctgag gagagaggga cctgggtaag            50

<210> SEQ ID NO 163
<211> LENGTH: 50
<212> TYPE: DNA
<213> ORGANISM: Homo sapiens

<400> SEQUENCE: 163
cgccctccgc ggccgcccgg cgcgagctcc cgggcggggc gctgtccagc            50

<210> SEQ ID NO 164
<211> LENGTH: 50
<212> TYPE: DNA
<213> ORGANISM: Homo sapiens

<400> SEQUENCE: 164
gtgatggtcg gaggatagtt gactgtgacc agcacgcggc ggctgtcggg            50

<210> SEQ ID NO 165
<211> LENGTH: 50
<212> TYPE: DNA
<213> ORGANISM: Homo sapiens

<400> SEQUENCE: 165
cgccgagtta accccgttgt gagtcacgca ctcatactcc ccggcctggc            50

```
<210> SEQ ID NO 166
<211> LENGTH: 50
<212> TYPE: DNA
<213> ORGANISM: Homo sapiens

<400> SEQUENCE: 166
gcagccgcac ccgcgggtcc ctggtcctgc ggtcgttgcc ggcgtacagg          50

<210> SEQ ID NO 167
<211> LENGTH: 50
<212> TYPE: DNA
<213> ORGANISM: Homo sapiens

<400> SEQUENCE: 167
ccgcgcgcag cgaccgatgc cttgcatgca acatgcaacg ggcccgacgg          50

<210> SEQ ID NO 168
<211> LENGTH: 50
<212> TYPE: DNA
<213> ORGANISM: Homo sapiens

<400> SEQUENCE: 168 gcagggatg cggacgccac cctggtccca cgcctccgcg gggcggctct           50

<210> SEQ ID NO 169
<211> LENGTH: 50
<212> TYPE: DNA
<213> ORGANISM: Homo sapiens

<400> SEQUENCE: 169
tggggtaggt gactctcgct agatccctcc aaagcagacc ggtggcgatg          50

<210> SEQ ID NO 170
<211> LENGTH: 50
<212> TYPE: DNA
<213> ORGANISM: Homo sapiens

<400> SEQUENCE: 170
ccggctcccc ggaccccgag cgcggccaga gagctgcgga gcccgagtgc          50

<210> SEQ ID NO 171
<211> LENGTH: 50
<212> TYPE: DNA
<213> ORGANISM: Homo sapiens

<400> SEQUENCE: 171
agagacgata ccgaaaccca atggaccgcg aggaccgaag gcagatccgg          50

<210> SEQ ID NO 172
<211> LENGTH: 50
<212> TYPE: DNA
<213> ORGANISM: Homo sapiens

<400> SEQUENCE: 172
gccgctgagc gccggcaggt tggaccagcg ctgcgcgccg gaagtgcact          50

<210> SEQ ID NO 173
<211> LENGTH: 50
<212> TYPE: DNA
<213> ORGANISM: Homo sapiens

<400> SEQUENCE: 173
atgtgcaggg ggtgcaggac tgtgtgcggg gctggagcga gtgtgcgggc          50
```

```
<210> SEQ ID NO 174
<211> LENGTH: 50
<212> TYPE: DNA
<213> ORGANISM: Homo sapiens

<400> SEQUENCE: 174
ttgcggttcg cggcgtgccg gacgtgacaa acggaagccg cacgtctcac          50

<210> SEQ ID NO 175
<211> LENGTH: 50
<212> TYPE: DNA
<213> ORGANISM: Homo sapiens

<400> SEQUENCE: 175
ggcggggtgc ggagcgggtg agggacccga gggtgtataa cggggggtag          50

<210> SEQ ID NO 176
<211> LENGTH: 50
<212> TYPE: DNA
<213> ORGANISM: Homo sapiens

<400> SEQUENCE: 176
ggtttgtaaa cactcggccc gacgccgggc cgcggaacgg aagcgcccgc          50
```